US012584837B2

(12) United States Patent　　　　(10) Patent No.: US 12,584,837 B2
Grenier et al.　　　　　　　　　　　(45) Date of Patent: Mar. 24, 2026

(54) DEVICE FOR MEASURING PHYSICOCHEMICAL PROPERTIES OF A DEFORMABLE MATRIX, IMPLEMENTATION METHOD AND USES

(71) Applicant: Institut national de recherche pour l'agriculture, l'alimentation et l'environnement, Paris (FR)

(72) Inventors: David Grenier, Ercé-Près-Liffré (FR); Antoine Lejeune, Louverné (FR); Tiphaine Lucas, Sens-de-Bretagne (FR); Yves Diascorn, L'Hermitage (FR)

(73) Assignee: Institut national de recherche pour l'agriculture, l'alimentation et l'environnement, Paris (FR)

( * ) Notice: Subject to any disclaimer, the term of this patent is extended or adjusted under 35 U.S.C. 154(b) by 256 days.

(21) Appl. No.: 17/924,988

(22) PCT Filed: May 11, 2021

(86) PCT No.: PCT/FR2021/050816
§ 371 (c)(1),
(2) Date: Nov. 11, 2022

(87) PCT Pub. No.: WO2021/229176
PCT Pub. Date: Nov. 18, 2021

(65) Prior Publication Data
US 2023/0184653 A1　　Jun. 15, 2023

(30) Foreign Application Priority Data
May 14, 2020　(FR) ...................................... 2004751

(51) Int. Cl.
*G01N 7/14*　　(2006.01)
*G01N 33/00*　　(2006.01)
(Continued)

(52) U.S. Cl.
CPC ........... *G01N 7/14* (2013.01); *G01N 33/0011* (2013.01); *G01N 33/0036* (2013.01);
(Continued)

(58) Field of Classification Search
None
See application file for complete search history.

(56) References Cited

U.S. PATENT DOCUMENTS 2,233,372 A　　2/1941　Baker et al.
3,849,070 A　*　11/1974　Garza ................... G01N 33/02
　　　　　　　　　　　　　　　　　　　　　422/68.1
(Continued)

FOREIGN PATENT DOCUMENTS

EP　　　0422260 A1　　4/1991
EP　　　0687900 A1　　12/1995
WO　　2021229176 A1　　11/2021

OTHER PUBLICATIONS

Foreign Communication from a Related Counterpart Application, International Search Report dated Aug. 26, 2021, International Application No. PCT/FR2021/050816 filed on May 11, 2021.
(Continued)

*Primary Examiner* — Mark A Shabman
(74) *Attorney, Agent, or Firm* — Conley Rose, P.C.

(57) ABSTRACT

Disclosed herein is a device for measuring physicochemical properties with regard to gases in contact with a material, especially material transport properties with regard to gases in contact with a material and mechanical properties, comprising:
　an upper end, in which a pressure sensor connected to an apparatus for recording and optionally processing a signal is hermetically inserted;
　a lower end in communication with the pressure sensor and which is open in order to allow (i) insertion of the measuring device into the material and (ii) formation of
(Continued)

a gaseous chamber between the pressure sensor and the material when the measuring device is inserted therein;

a system for scavenging a gas;

at least one means for introducing the gas into the device, and advantageously at least one means for removing the gas from the device;

the device made from a material which does not absorb the gas.

20 Claims, 18 Drawing Sheets

(51) Int. Cl.

| | | |
|---|---|---|
| *G01N 33/02* | (2006.01) | |
| *G01N 33/24* | (2006.01) | |
| *G01N 33/38* | (2006.01) | |
| *G01N 33/46* | (2006.01) | |

(52) U.S. Cl.

CPC ............. *G01N 33/02* (2013.01); *G01N 33/24* (2013.01); *G01N 33/38* (2013.01); *G01N 33/46* (2013.01)

(56) References Cited

U.S. PATENT DOCUMENTS

| | | | | |
|---|---|---|---|---|
| 4,702,102 | A * | 10/1987 | Hammerton | G01N 7/10 96/417 |
| 5,099,679 | A * | 3/1992 | Huerlimann | G01N 1/2226 73/52 |
| 5,212,993 | A * | 5/1993 | Mayer | G01N 1/2226 73/52 |
| 2016/0327456 | A1* | 11/2016 | Zimbron | G01N 1/2214 |
| 2016/0348561 | A1* | 12/2016 | Higashi | F01N 11/007 |

OTHER PUBLICATIONS

Foreign Communication from a Related Counterpart Application, Written Opinion dated Aug. 26, 2021, International Application No. PCT/FR2021/050816 filed on May 11, 2021.

Rzigue Asma, et al.: "Bread collapse. Causes of the technological defect and impact of depanning time on bread quality", Journal of Food Engineering, Barking Essex, GB, vol. 182, Mar. 17, 2016, pp. 72-80, XP029488952, DOI: 10.1016/J.JFOODENG.2016.03.007.

Huc et al.: "Influence of salt content on eye growth in semi-hard cheese studied using magnetic resonance imaging and CO2 production measurements", International Dairy Journal (2014).

Acerbi et al.: "Impact of salt concentration, ripening temperature and ripening time on CO2 production of semi-hard cheese with propionic acid fermentation", Journal of Food Engineering, 177, 72-79 (2016).

Tveteraas O.: "A study of pressure decay in a closed CO2-water system", Master Thesis, 2011.

Ghaderi et al.: "Estimation of concentration-dependent diffusion coefficient in pressure-decay experiment of heavy oils and bitumen", Fluid phase equilibria, 2011.

Acerbi et al.: "An appraisal of the impact of compositional and ripening parameters on CO2 diffusivity in semi-hard cheese", Food Chemistry, 2016.

Chaix E.: "Caractérisation et modelisation des transferts de gaz (O2/CO2) dans le système emballage/aliment en lien avec les reactions de croissance microbienne (microbiologie prévisionnelle) (Characterization and modeling of the gas transfers (O2/CO2) in the packaging/food system in relation to the microbial growth reactions (predictive Microbiology))", Thesis of the University of Montpellier 2, 2014 [p. 123 paragraph 2].

Chaix et al.: "Oxygen and carbon dioxide solubility and diffusivity in solid food matrix: a review of past and current knowledge", Comprehensive reviews in food science and food safety, Chaix et al., 2014.

Jakobsen M., Nygaard Jensen P.: "Assessment of carbon dioxide solubility coefficients for semi-hard cheeses: the effect of temperature and fat content", Eur. Food Res. Technol., 229, 287-294 (2009).

Grenier D., Laridon Y., Le Ray D., Challois S., Lucas T.: "Monitoring of single eye growth under known gas pressure: Magnetic resonance imaging measurements and insights into the mechanical behavior of a semi-hard cheese", Journal of Food Engineering 171, 119-128, (2016).

Bloksma, A., Nieman, W., (1975), "The effect of temperature on some rheological properties of wheat flour doughs", Journal of Texture studies 6(3), 343-361.

Mouazen, M., (2011), "Evolution des propriétés rheologiques des enrobés bitume, vers une loi vieillissement/viscosité. (Evolution of the rheological properties of coated bitumen, towards an aging/viscosity law)", École Nationale Supérieure des Mines de Paris (Higher National School of Mines, Paris) [Table 11 at p. 63].

Moultos, O.A., Tsimpanogiannis, I.N., Panagiotopoulos, A.Z., Economou, I.G., (2014), "Atomistic molecular dynamics simulations of CO2 diffusivity in H2O for a wide range of temperatures and pressures", The Journal of Physical Chemistry B 118(20), 5532-5541.

Sander, R., (2015), "Compilation of Henry's law constants (version 4.0) for water as solvent", Atmospheric Chemistry and Physics 15(8), 4399-4981.

Versteeg, G.F., Van Swaaij, W.P., (1988), "Solubility and diffusivity of acid gases (carbon dioxide, nitrous oxide) in aqueous alkanolamine solutions", Journal of Chemical & Engineering Data 33(1), 29-34.

* cited by examiner

DEVICE FOR MEASURING PHYSICOCHEMICAL PROPERTIES OF A DEFORMABLE MATRIX, IMPLEMENTATION METHOD AND USES

CROSS-REFERENCE TO RELATED APPLICATIONS

The present application is a filing under 35 U.S.C. 371 as the National Stage of International Application No. PCT/FR2021/050816, filed May 11, 2021, entitled "DEVICE FOR MEASURING PHYSICOCHEMICAL PROPERTIES OF A DEFORMABLE MATRIX, IMPLEMENTATION METHOD AND USES," which claims priority to French Application No. 2004751 filed with the Intellectual Property Office of France on May 14, 2020, both of which are incorporated herein by reference in their entirety for all purposes.

TECHNICAL FIELD

The present invention relates to a device for measuring physicochemical properties of a material with regard to gas, to a method for measuring the pressure of a gas in contact with a material, using the measuring device as well as to the use of the device for measuring, in a material, at least one physicochemical property with regard to gases selected from among material transport properties and mechanical properties.

The present invention is especially applicable in the agri-food and building fields.

In the following description, the references between square brackets ([ ]) refer to the list of references provided at the end of the document.

PRIOR ART

Knowledge of the physicochemical properties of the deformable matrices with regard to gas, in particular carbon dioxide ($CO_2$), is important for optimizing their production methods and for ensuring the quality of the end product.

Irrespective of the technical field to which these deformable matrices belong, determining these properties currently remains time consuming and expensive, since it involves setting up specific and independent series of experiments for each property, involving various analytical methods, such as chemical assays (Acerbi et al.: "Impact of salt concentration, ripening temperature and ripening time on CO2 production of semi-hard cheese with propionic acid fermentation", Journal of Food Engineering (2016) ([2]); Jakobsen M., Nygaard Jensen P.: "Assessment of carbon dioxide solubility coefficients for semi-hard cheeses: the effect of temperature and fat content", Eur. Food Res. Technol., 229, 287-294 (2009) ([8])) or electrochemical methods (Chaix et al.: "Oxygen and carbon dioxide solubility and diffusivity in solid food matrix: a review of past and current knowledge", Comprehensive reviews in food science and food safety (2014) ([7])), measurements by infrared spectroscopy (Chaix et al. ([7])) or even by chromatography (Chaix et al. ([7])). These properties can also evolve over time, making their measurement even more tedious. Furthermore, they make it difficult to perform "core" (in situ) measurements, since they require the removal of one or more end(s) of the food matrix, resulting in measurement uncertainty due to the food matrix coming into contact with the ambient atmosphere. In the case of food matrices, such as breads, pastries or cheeses, the microorganisms of the food matrix are then exposed to the oxygen in the air, and the gases initially solubilized in the matrix desolubilize almost instantaneously on the surface, thereby modifying the measured parameters compared to what they were in situ.

Thus, a tool does not currently exist that is capable of quickly measuring, especially in food matrices, various physicochemical parameters of these matrices with regard to gas.

Therefore, a genuine need exists for devices and methods making it possible to measure various physicochemical properties of a deformable matrix overcoming these defects, disadvantages and obstacles of the prior art.

DESCRIPTION OF THE INVENTION

The inventors have been able to address these requirements by developing a measuring device that allows the aforementioned problems to be overcome, with the original operating principle of said device being based on the measurement of the pressure variations in a gaseous phase in contact with a matrix, especially a food matrix, following various pressure stresses, over durations ranging from a few minutes to a few hours, or even a few days, depending on the parameters to be measured. Thus, advantageously, a single type of measurement is required to determine all the desired physicochemical properties.

The operating principle of the probe involves measuring pressure variations in a gaseous phase in contact with the matrix to be analyzed following various pressure stresses over durations ranging from a few minutes to a few hours, optionally a few days, preferably without exceeding 4 days, depending on the parameters to be measured. Thus, a single type of measurement is required to determine all the desired physicochemical properties. The originality of the probe is based on the implementation of a gas scavenging system in order to ensure that the environment is only made up of this gas. Furthermore, the probe allows core measurements to be taken.

In addition, the technical features of the device of the invention allow faster and core (in situ) measurements to be taken, which is an improvement compared to the methods that are conventionally used, which require sampling a piece from the matrix and bringing it into contact with the ambient atmosphere, which can modify its properties. The results obtained by implementing the device of the invention are therefore more relevant than those measured after taking samples of matrix pieces.

Furthermore, the ease of use of the device of the invention, its compactness and its measurement speed are all advantages for manufacturers. They especially allow the properties to be assessed on site, for example, on wheels in the process of ripening, on a bread dough during fermentation or even when manufacturing a cement slab.

Moreover, using a single apparatus for measuring various, or even all the physicochemical properties, obviates the costly purchase of other tools and specific training of the user on each of these tools.

All these properties also can be used for monitoring production methods and also in research and development centers. They are all used to understand and model the growth of bubbles, for example, in cheese where the number, the distribution and the size of the bubbles are important selection criteria for consumers. Finally, the solubility and the diffusion of the gases, especially of $CO_2$, are useful for selecting the packaging for foodstuffs.

Thus, a first aim of the invention relates to a device for measuring physicochemical properties with regard to gas in contact with a material, comprising:

an upper end, in which a pressure sensor connected to an apparatus for recording and optionally processing a signal is hermetically inserted;

a lower end, which is in communication with said pressure sensor and which is open to allow (i) the measuring device to be inserted into the material and to allow (ii) a gaseous chamber to be formed between said pressure sensor and the material when said measuring device is inserted therein;

a single gas scavenging system;

at least one means for introducing said gas into the device, and advantageously at least one means for removing said gas from the device;

said device being made from a material that does not absorb said gas.

Within the meaning of the present invention, "material" is understood to mean any material in which at least one gas is likely to solubilize and diffuse. Thus, the material can be a deformable material. The material can be cellular or non-cellular. Furthermore, it can be a food matrix, or a non-food matrix. In the case of a food matrix, it can be, for example, a matrix selected from among a cheese product, a bakery product, such as a bread dough, a meat, a fish, a meat or fish based product, a fruit, a vegetable, a fruit or vegetable based product, a food paste, and the mixtures thereof. In the case of a non-food matrix, it can be, for example, a matrix selected from among bitumen, concrete, cement, asphalt, plaster, polymers, gels, earth, wood, silicone, coal, rocks, and mixtures thereof.

Within the meaning of the present invention, "physicochemical properties" is understood to mean any material transport property with regard to gas, as well as the mechanical properties. Advantageously, the material transport properties can be selected from among the diffusion coefficient, the gaseous gas/dissolved gas equilibrium constant, the dissolved gas concentration and/or the production rate. The mechanical properties can be selected from among the elasticity, the viscosity, the visco-elasticity and the fracture point.

Advantageously, the gas for which the physicochemical properties of the material need to be determined can be any gas likely to solubilize and diffuse in the material. It can be, for example, a gas produced by the material itself, for example, in the case of a fermentable food matrix. It especially can be a gas selected from among carbon dioxide, nitrogen, oxygen, rare gases, volatile organic compounds, ammonia, and a mixture thereof.

The device of the invention is made of a material that does not absorb said gas for which the physicochemical properties of the material need to be determined. Indeed, this is necessary so as not to bias the measurements. It can be a material selected from among metal, glass and polymer materials previously saturated in said gas or treated so as not to absorb this gas. In any case, plastic materials not previously saturated in said gas or not previously treated so as not to absorb this gas are prohibited since they absorb certain gases, such as $CO_2$.

The device can assume any suitable shape as a function of the desired use and of the relevant material. In this respect, a person skilled in the art will know how to adapt this feature in view of their general knowledge. This can be, for example, a hollow tube, which can be cylindrical, oval or polygonal, for example, square, rectangular or hexagonal. Preferably, the device is a hollow tube, optionally cylindrical.

The size of the device can be selected as a function of the desired use and of the relevant material. In this respect, a person skilled in the art will know how to adapt this feature in view of their general knowledge. For example, the device can be a portable device or a fixed device. Advantageously:

The height of the device can be at least a few millimeters, or even a few tens of millimeters, in order to be able to easily insert the "core" probe into the material. The height of the device thus can be greater than or equal to 5 mm, for example, approximately 10 mm, or approximately 20 mm, or approximately 30 mm, or approximately 40 mm, or approximately 50 mm, or even greater than 50 mm, depending on the use thereof.

The height between the lower end of the device and the pressure sensor is advantageously greater than or equal to 1 mm, so as to be able to easily "plant" the device in the material over a minimum height of 1 mm in order to comply with certain computation hypotheses for data processing. For example, this height can range between 1 and 8 mm, or even can be greater than 8 mm, as previously indicated.

The diameter of the device can be the same over the entire length of the device, or can be substantially the same. It is preferably of the order of a few millimeters, for example, between 2 and 10 mm, in order to quickly acquire the desired data. Optionally, the diameter can be greater than 10 mm. Advantageously, the diameter of the device can be selected as a function of the desired duration of an analysis; indeed, in general, the smaller the volume of the gaseous chamber, the faster certain analyses.

Advantageously, the height of the device can be greater than or equal to 5 mm, and the height between the lower end of the device and the pressure sensor is greater than 1 mm.

Within the meaning of the present invention, "lower end" is understood to mean the end of the device intended to be in contact with the material. Furthermore, it is open to allow the device to be pushed into the material.

Within the meaning of the present invention, "upper end" is understood to mean the end of the device that is opposite the lower end, and that is not intended to be in contact with the material. Thus, advantageously, only the lower end of the device of the invention is inserted into the material, and not the upper end. As previously indicated, the device comprises a pressure sensor hermetically inserted into the upper end of the device, so as to control the pressure in the gaseous chamber that is formed between the pressure sensor and the material when the measuring device is inserted therein. Thus, there are no unwanted gaseous exchanges between the gaseous chamber and the ambient air, outside the device. To this end, the gas-tightness can be provided by any known means, for example, a weld between the pressure sensor and the walls of the device.

The pressure sensor can be any commercially available sensor for measuring the force exerted by the gases and that is able to be adapted to the device of the invention. It can be, for example, the pressure sensor by Kulite Semiconductor Products Inc., model XCQ-093-1.7.BARA.

The recording apparatus to which the pressure sensor is connected can be any commercially available apparatus as long as it can be adapted to the pressure sensor that is used. Advantageously, but optionally, the recording apparatus can also process the received signal, that is, electronically correct the magnitudes of error such as the offset, the sensitivity, the temperature effect on the offset, the effect of the temperature on the sensitivity, non-linearity and hysteresis.

Advantageously, the recording apparatus can process the signal in order to provide the numerical values of the physicochemical properties to be determined. Alternatively, the signal processing can be conducted manually or subsequently, in the case whereby the sensor has no signal processing function.

The device of the invention can be inserted into the material by pushing the lower end of the device directly into the material when allowed thereby, or else into a hole previously made in the material when the material is too firm. This hole can be produced using any suitable tool, such as a drill bit, for example. The depth of the hole depends on the considered material and will be determined by a person skilled in the art in view of their general technical knowledge. For example, the depth of the hole can range between 1 mm and 80 mm, especially for materials of the food paste type such as cheese. Once inserted into the material, the space formed between the material and the upper end, which is hermetically sealed, of the device is called "gaseous chamber".

Advantageously, the gas scavenging system allows a gas to be introduced into the gaseous chamber in order to remove the gas already present therein, so that the environment of the gaseous chamber is solely made up of this gas. The gas used to this end can be any gas conventionally used in gas scavenging systems of industrial or food equipment, for example, $CO_2$, nitrogen or argon, or even the gas for which the material transport properties are intended to be determined. Advantageously, for the measurements of the mechanical properties, any gas can be used, and preferably a gas that does not dissolve or that hardly dissolves, such as $CO_2$, nitrogen or argon. For the measurements of the material transport properties, the gas for which the material transport properties are intended to be determined is preferably used. The scavenging system can be a commercially available system, for example, a gas cylinder.

The gas scavenging system is connected to at least one gas intake means. This intake means can be located over the entire height of the device, for example, either in the upper part of the device, and/or in the lower part of the device. This intake can be provided by any means conventionally used to this end, such as an orifice, for example. Advantageously, the gas intake, and optionally its flow rate, can be controlled by a suitable device, for example, a valve, able to be opened or closed depending on the requirements of the user. Thus, as can be seen from the above explanations, the gas intake means is connected to an external gas source, such as a gas cylinder, syringe or a pouch, with this list being by no means limiting. Furthermore, according to the invention, the gas intake means is not a means for sampling the gas included in the material. The device of the invention also comprises at least one gas outlet means. This outlet means can be located over the entire height of the device, for example, either in the upper part of the device, and/or in the lower part of the device. This outlet can be provided by any means conventionally used to this end, such as an orifice, for example. Advantageously, the gas outlet, and optionally its flow rate, can be controlled by a suitable device, for example, a valve, able to be opened or closed depending on the requirements of the user.

Advantageously, the device of the invention can comprise at least one temperature sensor making it possible to measure the temperature in the gaseous chamber. This sensor can be useful, especially when the temperature is likely to vary during measuring. To this end, any suitable and commercially available temperature sensor can be used.

In one embodiment compatible with all the features as defined above, the device of the invention can comprise an extension sealably connected with the lower end of said device. Advantageously, the extension can be made of a material as defined above for the device. It can be the same material as that forming the rest of the device, or it can be another material as defined above. The extension can assume a shape that is similar to that of the rest of the device, for example, a hollow tube, the top of which is open in order to communicate with the rest of the device. The seal between the device and the extension can be provided by any means known to a person skilled in the art, for example, by a seal, a screwing system or a weld. The seal between the extension and the matrix to be analyzed can be provided by any means known to a person skilled in the art, for example, a seal or a screwing system. This embodiment is particularly useful for carrying out measurements of the mechanical properties of the material. The extension must have an aeration or any other system allowing through the gas. Thus, the extension advantageously can be perforated on at least one side and/or can be perforated at its lower end, in order to allow through the gas.

The device of the invention can further comprise at least one means for holding the device in position relative to said material, using any means adapted to this function known to a person skilled in the art, such as, for example, straps, clamps, or means for attaching to a bracket.

A further aim of the invention relates to a method for measuring the pressure of a gas in contact with a material, using a measuring device as defined above, comprising the following steps:

(a) inserting said measuring device into the material;
(b) optionally scavenging a gas from the gaseous chamber by means of the gas scavenging system at a constant pressure;
(c) varying the pressure of the gaseous chamber by means of the gas scavenging system to a desired pressure; and
(d) measuring the pressure and optionally the temperature of the gaseous chamber.

The step (a) of inserting the device can be conducted as indicated above. Advantageously, the insertion can be carried out at a depth of at least 1 mm. In any case, a person skilled in the art will know how to adapt the maximum depth as a function of the height between the lower end of the device and the pressure sensor, and as a function of tested material. The depth can range between 1 and 10 mm, for example.

The optional step (b) of scavenging a gas from the gaseous chamber by means of the gas scavenging system is carried out at a constant pressure, so that the pressure in the gaseous chamber does not substantially change. To this end, the means for introducing and removing the scavenging gas can be open. The time during which this step is carried out must be sufficient to allow the air present in the device to be replaced by the scavenge gas, and to achieve a constant pressure in the gaseous chamber, and it therefore depends on the volume of the gaseous chamber. This step also allows the initial pressure to be adjusted that is to be imposed for carrying out the measurements. By way of example, this duration can be at least 2 or 3 seconds, preferably without exceeding a few minutes. The pressure can be any pressure suitable for the measurement to be carried out, it can range between −1 kPa and +200 kPa (relative to atmospheric pressure), for example.

Step (c) of varying the pressure of the gaseous chamber by means of the gas scavenging system to a desired pressure can involve an increase or a reduction in the pressure of the gaseous chamber. This step is carried out after the step (a) of inserting the measuring device into the material, or after the step (b) of scavenging a gas from the gaseous chamber by means of the gas scavenging system at a constant pressure if said system is present. The desired pressure can be any pressure suitable for the measurement to be carried out. The increase or the reduction in pressure of step (c) can be carried out progressively until the material is fractured, especially when the parameter to be measured is the fracture point. For example, the increase or the reduction can be sufficient to reach a pressure ranging between −1 kPa and +200 kPa. In the case of an increase in the pressure, the scavenge gas intake means can be open in order to allow gas to enter the gaseous chamber, while the outlet means is closed to allow the pressure in the gaseous chamber to increase. In the case of a reduction in the pressure, the scavenge gas intake means can be closed and the outlet means open in order to allow gas to exit the gaseous chamber and thus allow the pressure in the gaseous chamber to reduce. Of course, pressure variations can be obtained using other methods, for example, by acting on the difference between the gas intake and outlet flow rates.

Step (d), which is carried out after the step of varying the pressure of the gaseous chamber, can be carried out for a duration that is adapted to the desired measurement. A person skilled in the art will know how to adapt this duration according to their general knowledge. For example, the measurement duration can range between a few minutes and a few days, for example, between 2 minutes and 3 days, or even more if necessary. The acquisition frequency of the pressure depends on the pressure variation, for example, according to the gas production rate by the material.

Advantageously, at least one step from among steps (b) and (c) can be carried out at least 2 times so as to monitor the evolution of the pressure over time.

Advantageously, the method of the invention can further comprise a step of calibrating the measurement as a function of the material and of the gas.

The average temperature at which the measurements are carried out can range between −20° C., in the case of cold preservation, and 200° C., in the case of a curing method. For example, the average temperature can be the ambient temperature, that is, approximately 20±1.5° C.

The number of measurements carried out depends on the requirements of the user. A person skilled in the art will know how to adapt this number, which can range between 1 and 10, for example, or even more if necessary. For example, in the case of a cheese, the number of measurements can depend on the number of ripening days.

Another aim of the invention relates to a use of a measurement device as defined above, for measuring, in particular in a material as defined above, at least one physicochemical property selected from among material transport properties with regard to gas and mechanical properties.

The material transport properties are selected from among the gas diffusion coefficient, the gaseous gas/dissolved gas equilibrium constant, the dissolved gas concentration and/or the production rate.

The mechanical properties are selected from among elasticity, viscosity, visco-elasticity and the fracture point.

Another aim of the invention relates to the use of a measuring device as defined above, for preparing or monitoring the features of materials in which a gas is likely to solubilize and diffuse. For example, these materials and these gases are as described above.

Especially, the device of the invention can be used as an alveograph for characterizing a material as defined above, for example, bread dough.

Other advantages may still become apparent to a person skilled in the art upon reading the following examples, which are illustrated by the appended figures and are provided by way of illustration.

Figure 1:
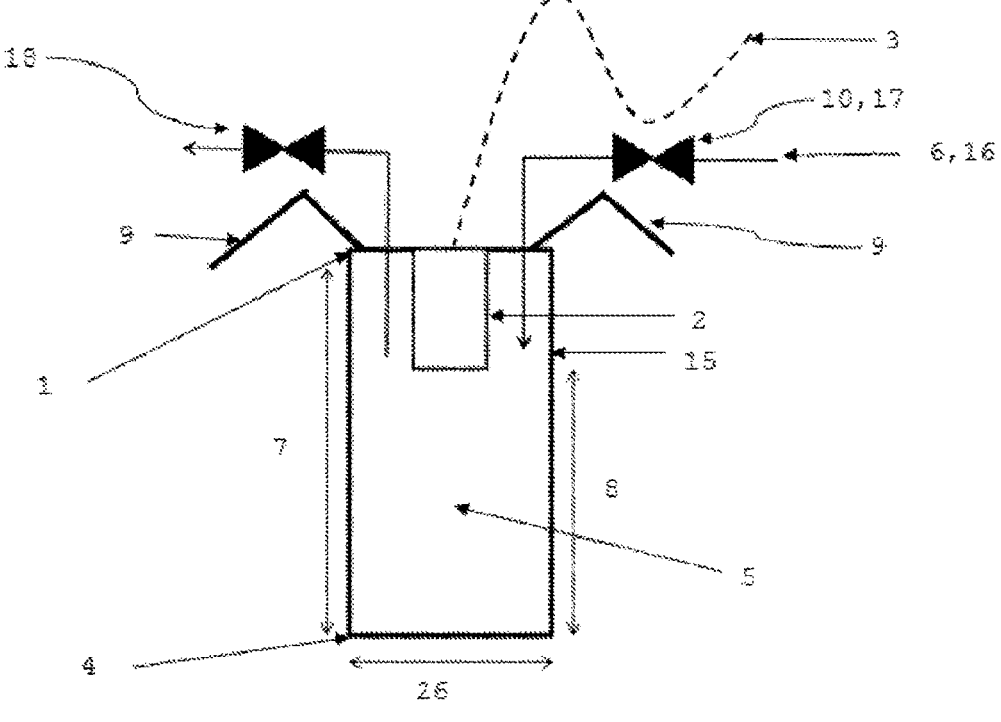
FIG. 1 shows the longitudinal cross-section of a schematic diagram of a measuring device according to the invention, also called "probe" hereafter.

A pressure sensor (2) (Kulite Semiconductor Products Inc., model XCQ-093-1.7.BARA) is inserted into a hollow cylindrical tube (15) of diameter (26) and of height (8), and that is preferably metal or glass, so as not to absorb $CO_2$. The pressure sensor (2) is connected to an apparatus (3) for processing and recording the signal.

The seal is ensured at the upper end (1) of the device by a weld produced between the pressure sensor (2) and the metal tube. The lower end (4) of the device is open since the tube (15) is hollow, and is in contact with the food matrix to be analyzed.

A $CO_2$ scavenging system (6), which is required to ensure that the environment is only made up of this gas, is also present. It is formed by a means (10) for introducing gas via the upper end (1) of the device, connected to a gas cylinder (16), and an outlet means (11) for discharging the gas.

A valve (17) allowing said gas to enter the device, and a valve (18) allowing said gas to exit from the device, allow the introduction/discharge of gas to be managed. The gas intake means (10) also allows the initial pressure to be adjusted that is to be imposed in order to carry out the measurements.

Finally, the device is provided with a means (9) for holding a food matrix in position in order to hold it in position during measurements, which means is made up of clamps in this embodiment.

In this embodiment, the device has the following dimensions: Height (7)=40 mm, height (8)=7 mm, Diameter (26)=3 mm.

In another embodiment, not shown in the figures, in order to take the measurements, $CO_2$ scavenging was carried out by conveying gas through the lower end (4) of the probe (only available opening) for at least 1 minute before it is planted into the cheese.

Figure 2:
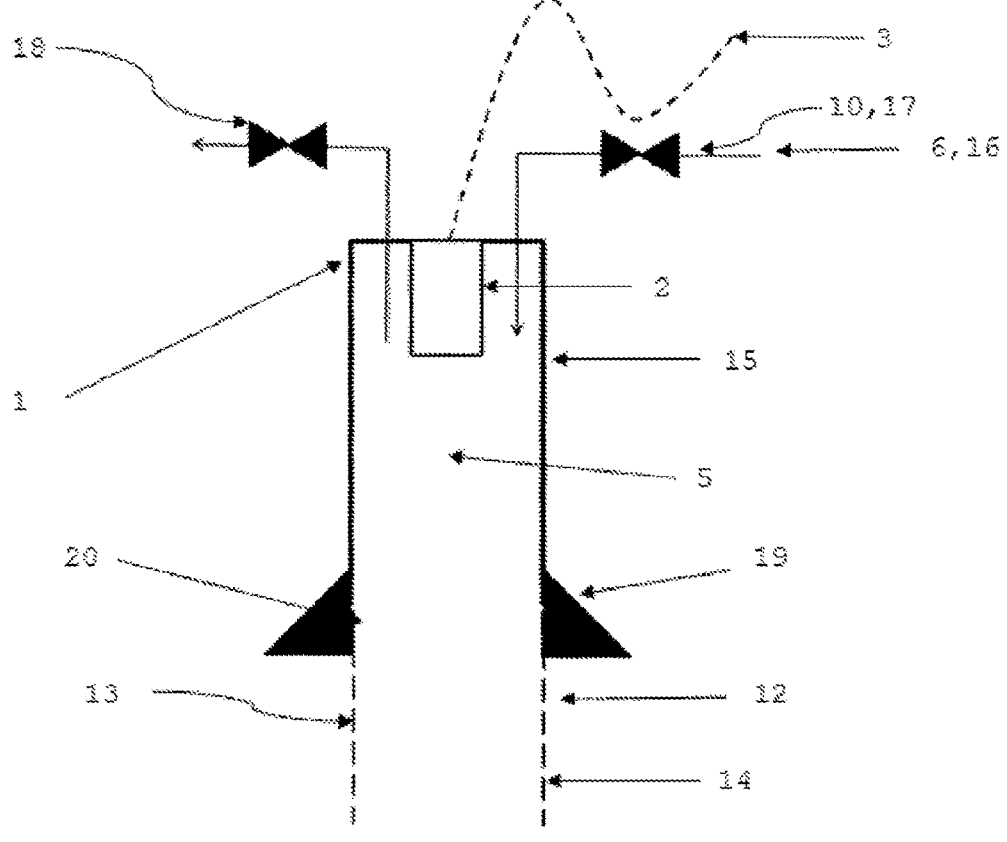

FIG. 2 shows the longitudinal cross-section of a schematic diagram of the measuring device of the type shown in FIG. 1, used with an extension (12). The extension (12) shown is made up of a hollow metal tube, the top (20) of which is open. This tube is optionally perforated on its sides (13) in order to let through the gas and/or is perforated at its lower end (14) in order to let through the gas. The extension (12) is also provided with a system (19) that provides the seal with the matrix to be analyzed (seal, screwing system, etc.). The extension (12) can be screwed, hooked to the rest of the probe.

Figure 3:
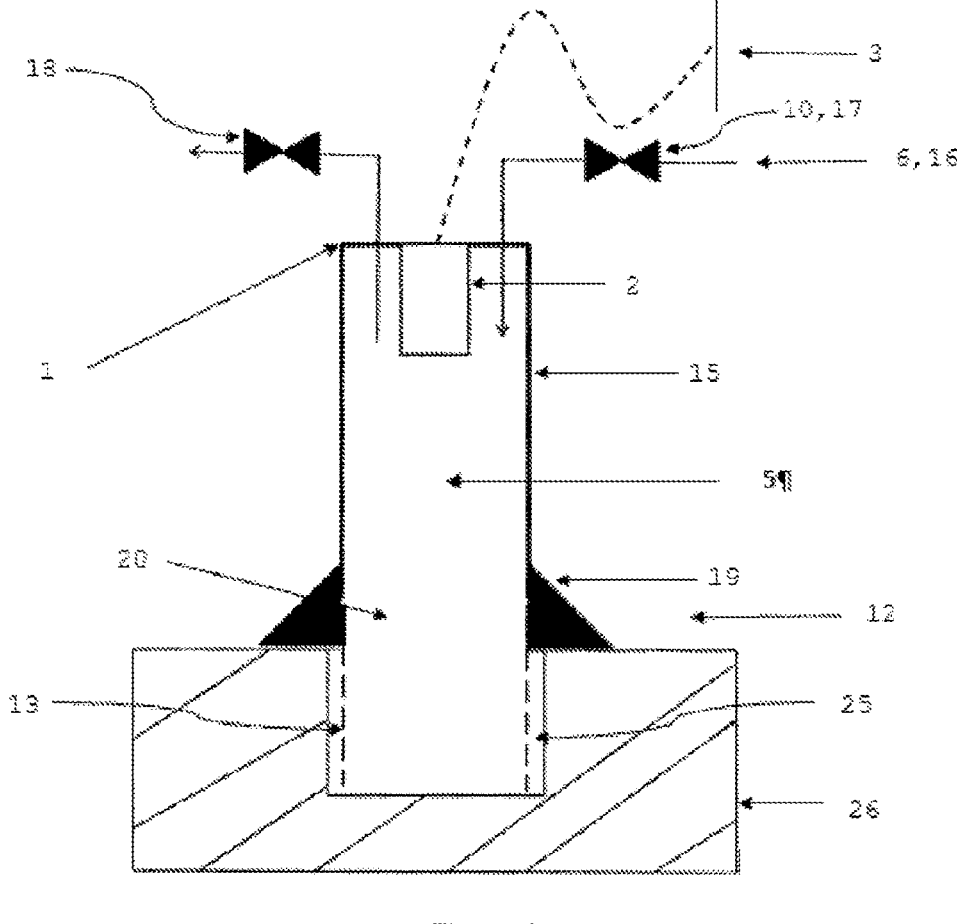
Figure 4:
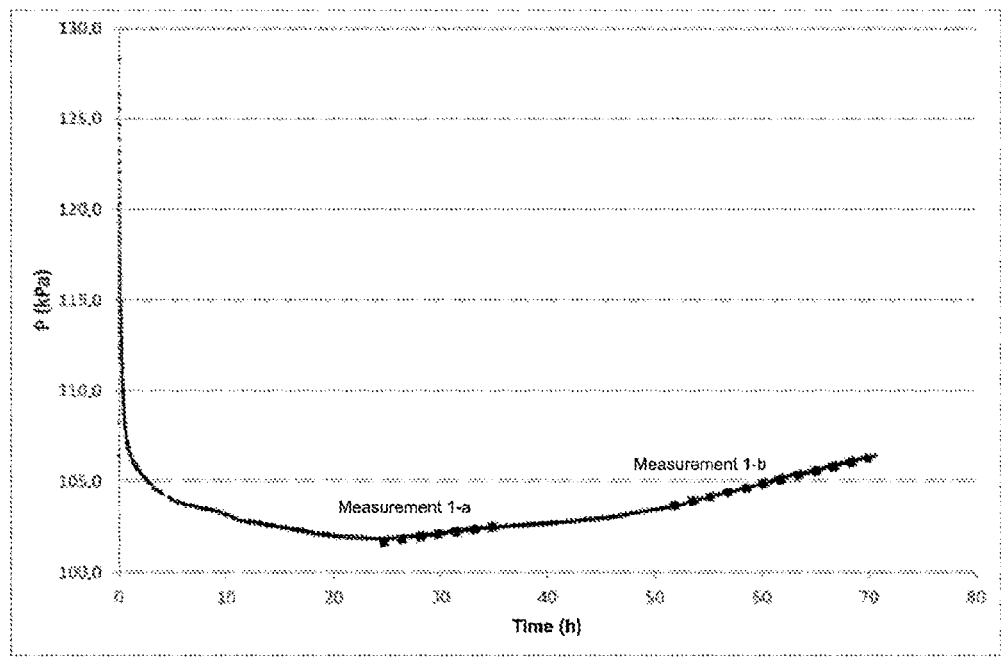
Figure 5:
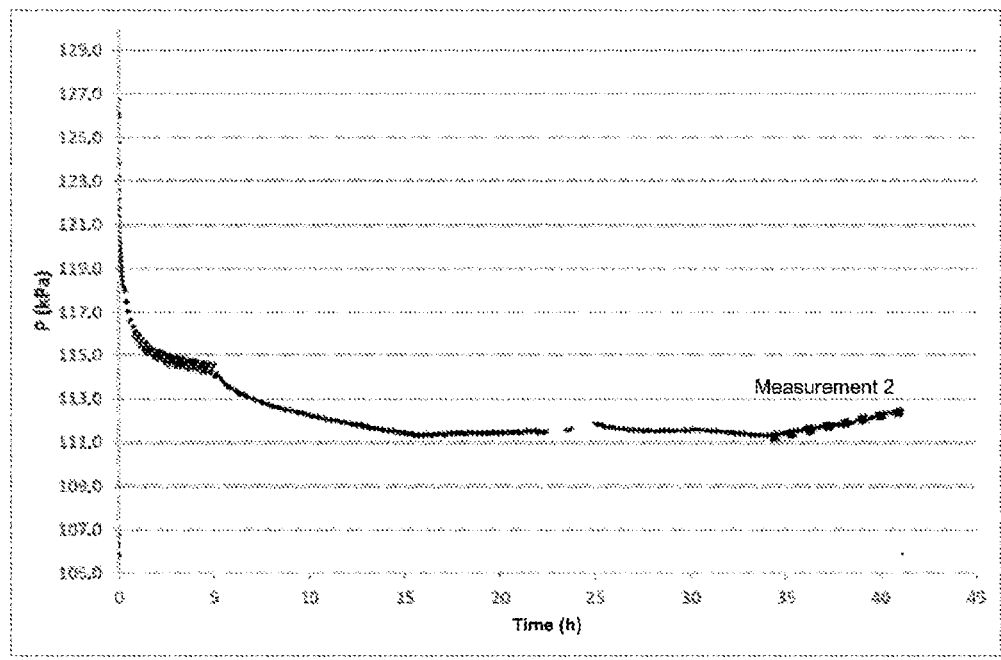
Figure 6:
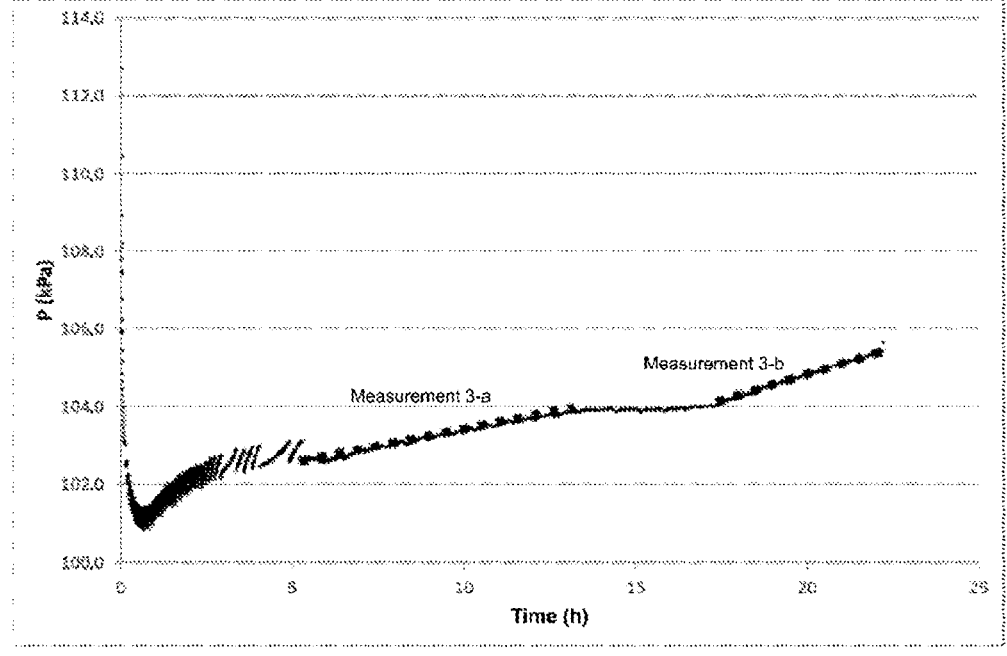
Figure 7:
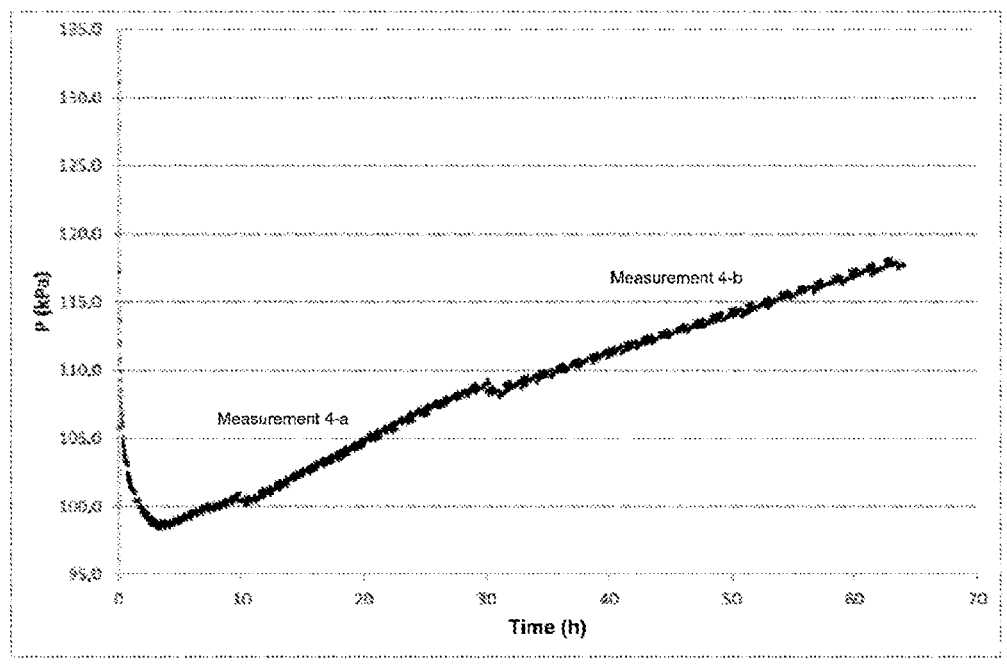

FIG. 3 shows the longitudinal cross-section of a schematic diagram of the measuring device used with an extension (12) of the type shown in FIG. 2, inserted into a cylindrical hole (25) made in the matrix (26) to be analyzed. It is inserted so that the sealing system (19) of the extension (12) is positioned in order to prevent gas leaks. A free gaseous chamber (5) is present between the surface of the matrix to be analyzed and the extension (12) of the probe. A gaseous space is formed in the hole (25) between the extension and the matrix.

FIGS. 4 to 7 show the results of the 4 pressure measurements (in kPa) (respectively FIG. 4, FIG. 5, FIG. 6 and FIG. 7) conducted as a function of time (hours). In each of these figures, straight lines have been drawn as dashed lines (respectively "Measurement 1*a*" and "Measurement 1*b*" in FIG. 4, "Measurement 2" in FIG. 5, "Measurement 3*a*" and "Measurement 3*b*" in FIG. 6 and "Measurement 4*a*" and "Measurement 4*b*" in FIG. 7) to symbolize the durations used to compute the $CO_2$ production rates.

Figure 8:
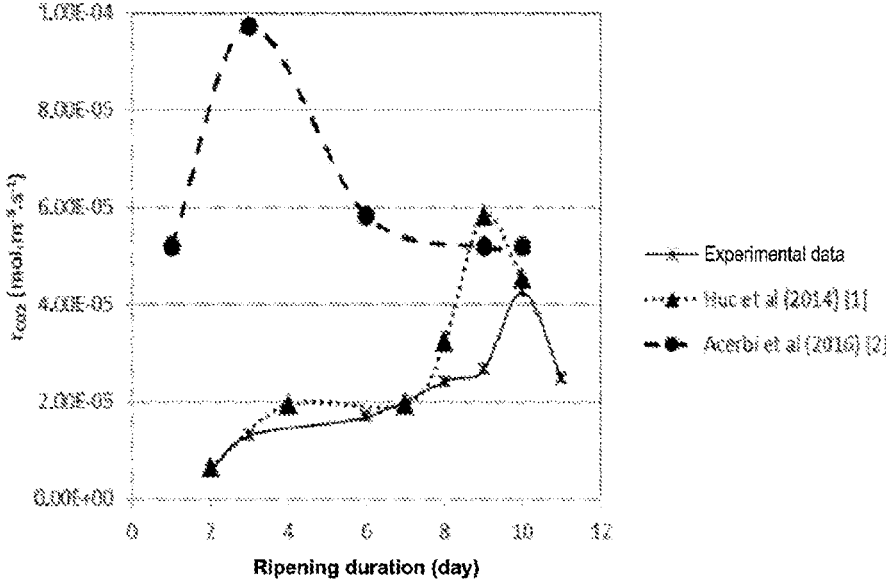

FIG. 8 shows the $CO_2$ production rate ($r_{CO2}$, by mol·m$^{-3}$·s$^{-1}$) by the cheese as a function of the ripening duration (in days), for the obtained experimental data (stars), the data mentioned in Huc et al. ([1]) (dotted line curve) and the data mentioned in Acerbi et al. ([2]) (dashed line curve).

Figure 9:
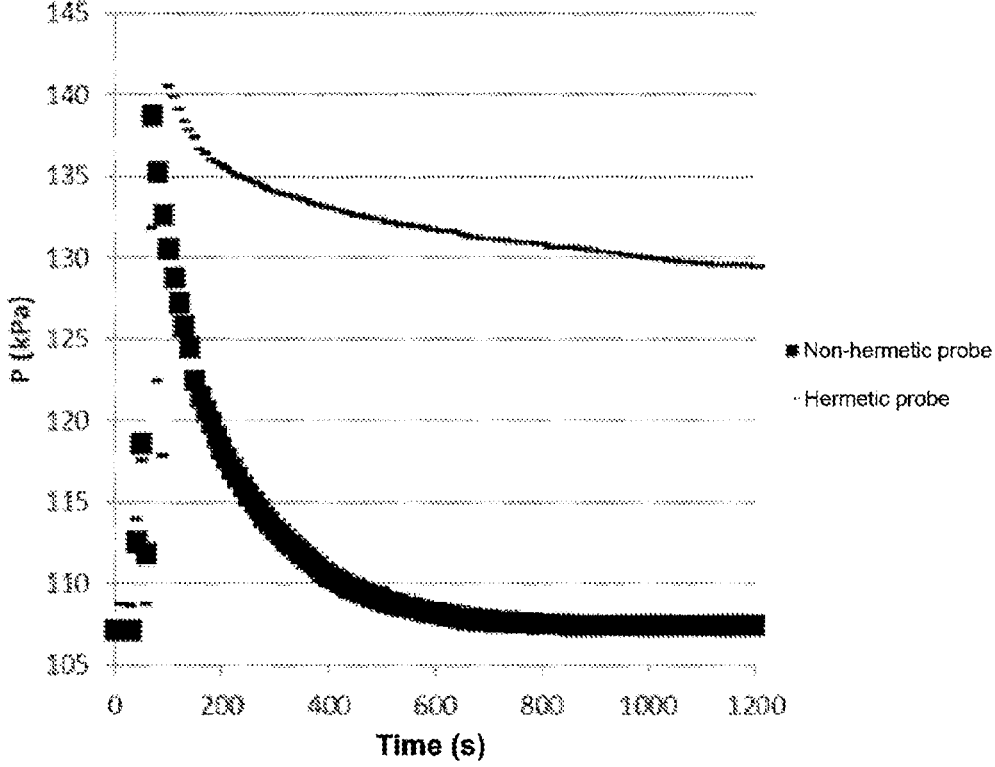

FIG. 9 shows the $CO_2$ pressure measurement (kPa) as a function of time (seconds) with a hermetic (dashes) or non-hermetic (squares) probe. It can be clearly seen that with a non-hermetic probe, the pressure reduction is much faster and that the pressure returns to its initial value after a few minutes.

Figure 10:
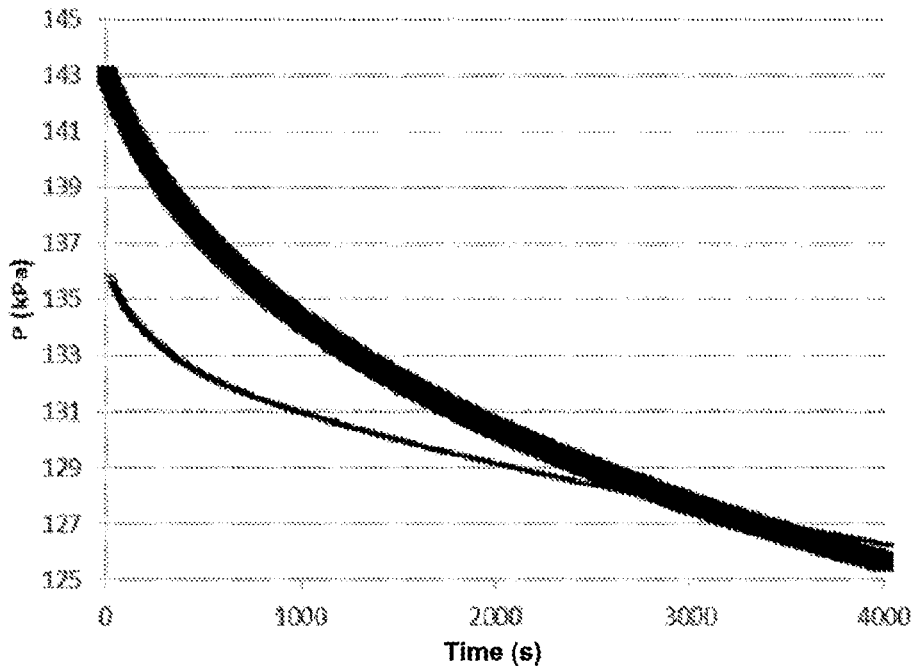

FIG. 10 shows the $CO_2$ pressure measurement (kPa) as a function of time (seconds) with the device of the invention with a piece of cheese (dashes) and without cheese with a plastic plug to close the lower end of the device (squares). It can be seen that with a plastic device, the $CO_2$ pressure quickly reduces due to the transfer of $CO_2$ into the plastic.

Figure 11:
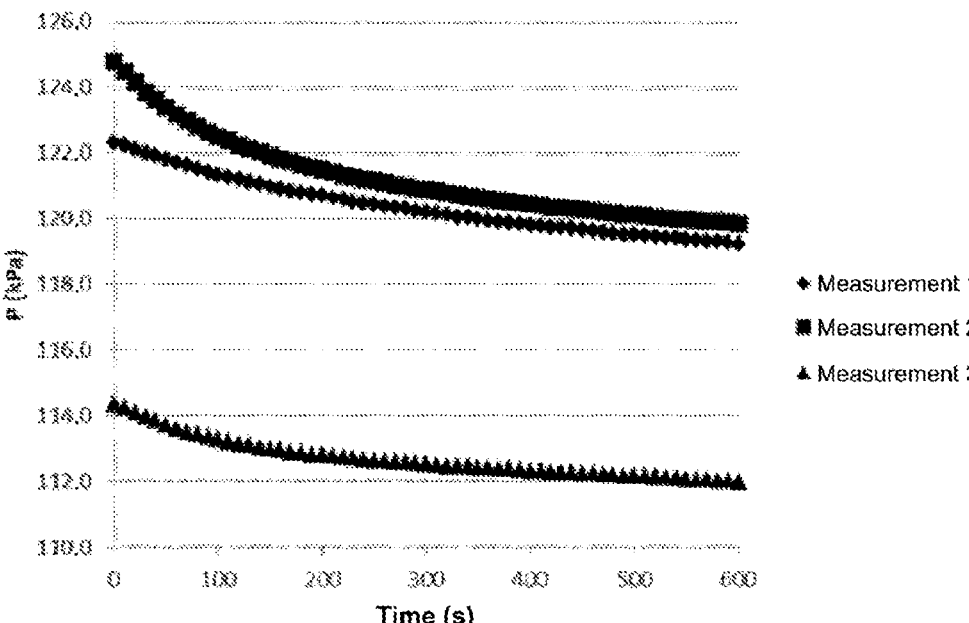

FIG. 11 shows the $CO_2$ pressure measurement (kPa) as a function of time (seconds), conducted 3 times, after an overpressure in the gaseous chamber in contact with the material. The measurements were carried out over a duration of approximately 10 min (600 s) with a pressure measurement every 10 seconds. Before taking the measurements, $CO_2$ had been scavenged from the gaseous chamber for approximately 1 minute.

Figure 12:
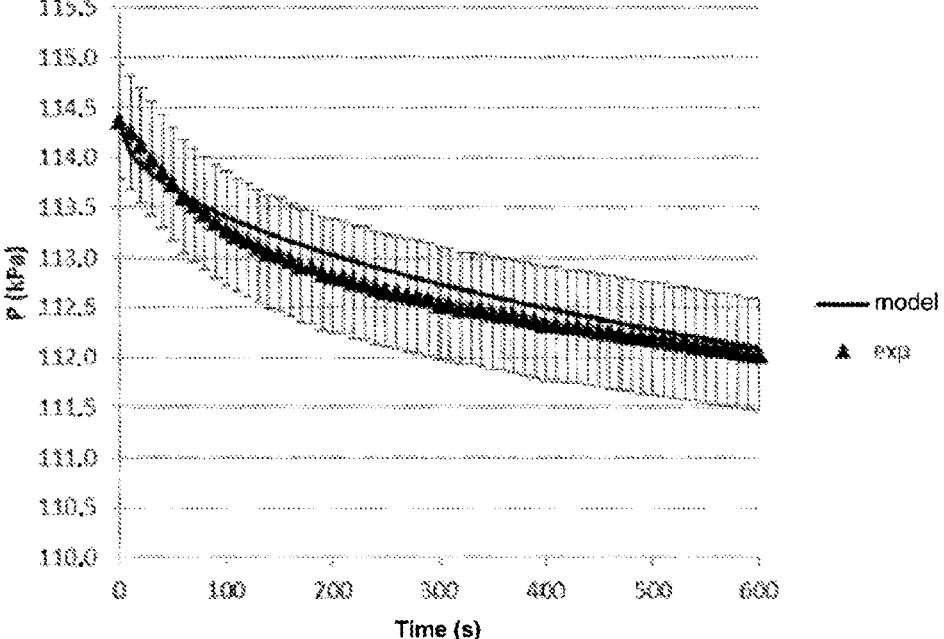

FIG. 12 shows the $CO_2$ pressure measurement (kPa) as a function of time (seconds), for the experimental data (Measurement 3, diamond line curve) compared with the model adjusted with Equation 2 ($D_{CO2}$=2.6×10$^{-10}$ m$^2$·s$^{-1}$). 0.5% error bars were used for the experimental values.

Figure 13:
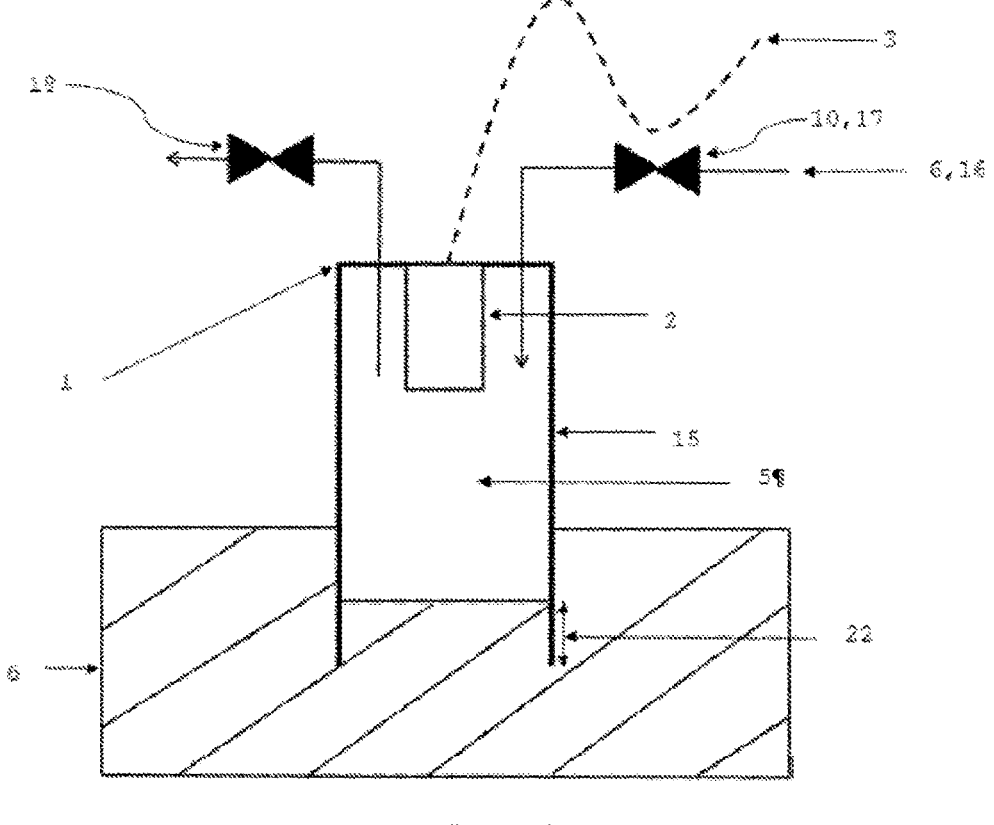

FIG. 13 shows the longitudinal cross-section of a schematic diagram of the measuring device of the type shown in FIG. 1, with the scavenging system (6) operating, that is with the gas intake valve (17) and the gas outlet valve (18) open. The device is planted in the matrix (26) to be analyzed at a height (22)>3 mm.

Figure 14:
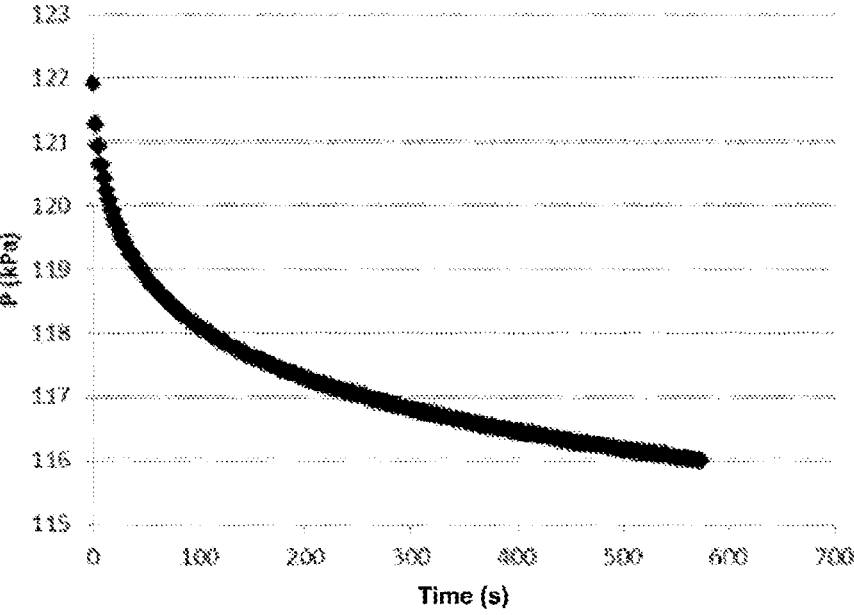

FIG. 14 shows an $N_2$ pressure measurement (kPa) as a function of time (seconds) for determining the viscosity of a cheese.

Figure 15:
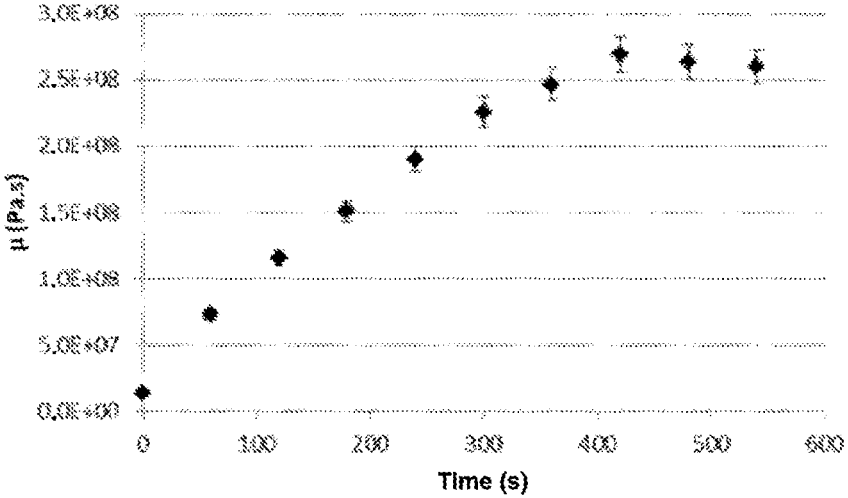

FIG. 15 shows the viscosity (Pa·s) computed with Equation 8 every minute when monitoring the pressure. It can be clearly seen that after a few minutes, the computed viscosity stabilizes because the material transfer becomes negligible.

Figure 16:
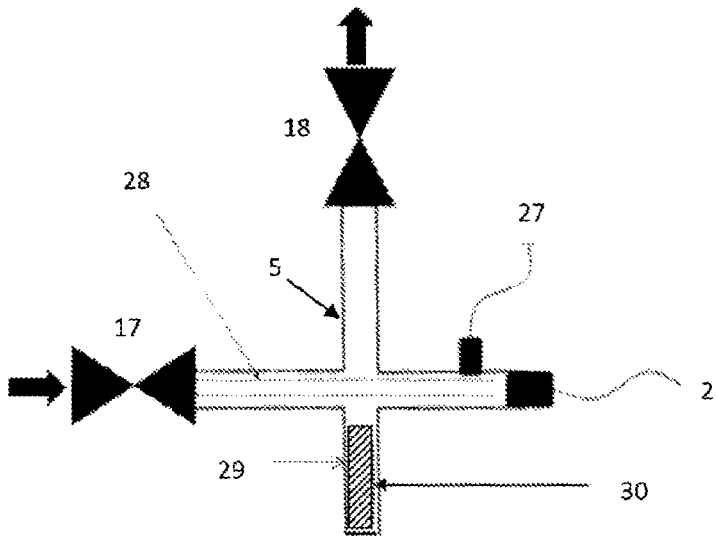

FIG. 16 shows a diagram of a measurement probe for determining the Henry constant (temperature sensor (27)–pressure sensor (2)).

Figure 17:
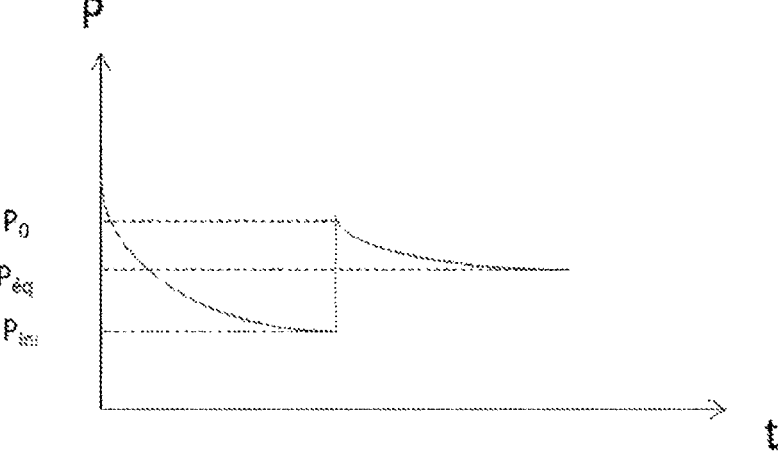

FIG. 17 shows the principle of the pressure variation for the measurement of the Henry constant.

Figure 18:
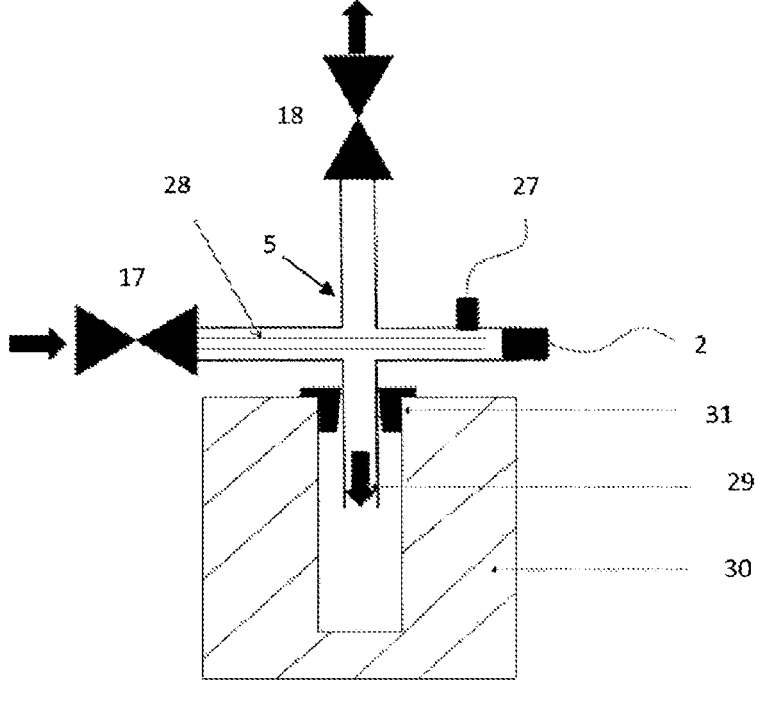

FIG. 18 shows a diagram of the measurement probe used to determine the viscosity (temperature sensor (27)–pressure sensor (2)).

Figure 19:
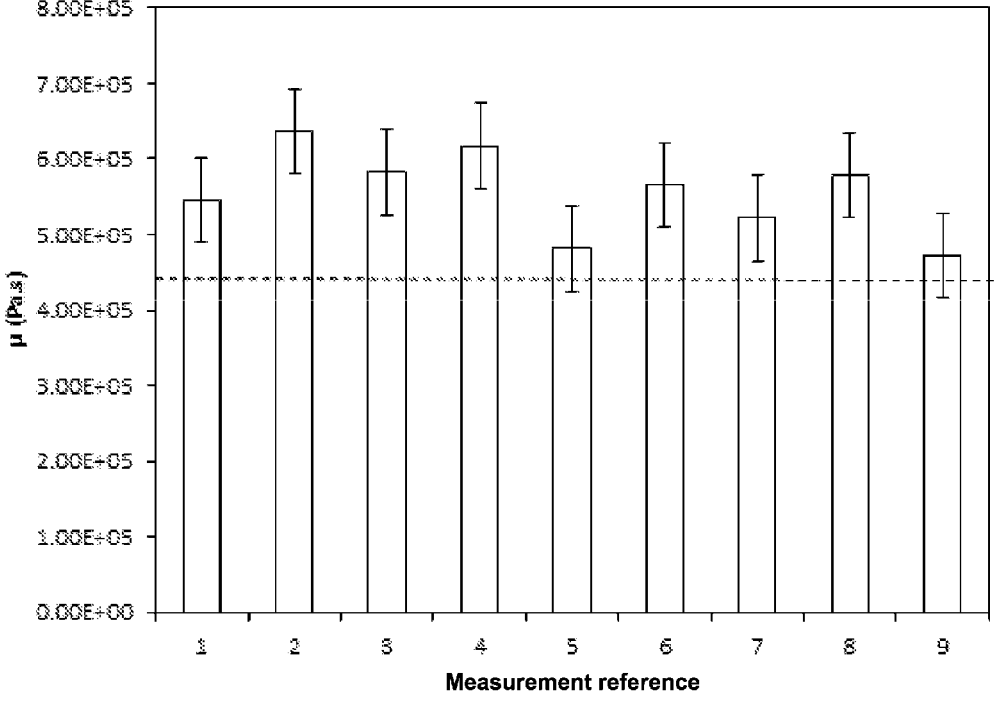

FIG. 19 shows the viscosity ($\mu$ in Pa·s) of the 70/100 Azalt bitumen determined with the probe (vertical bars, 9 measurements) and the value from the literature (dashed horizontal line).

10

Figure 20A:
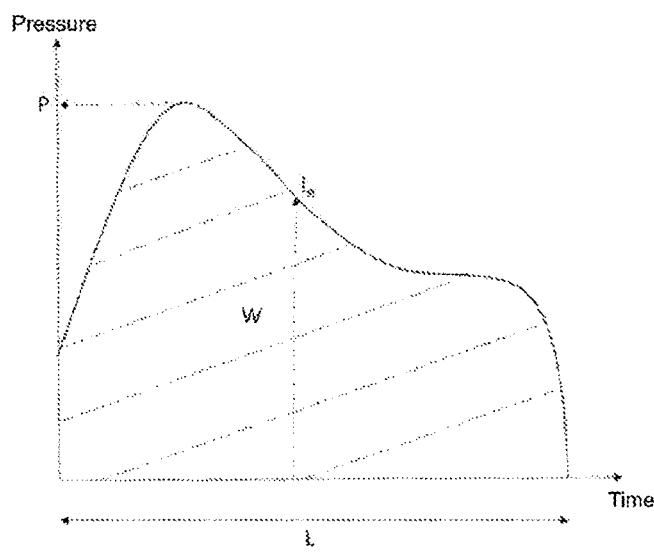
Figure 20B:
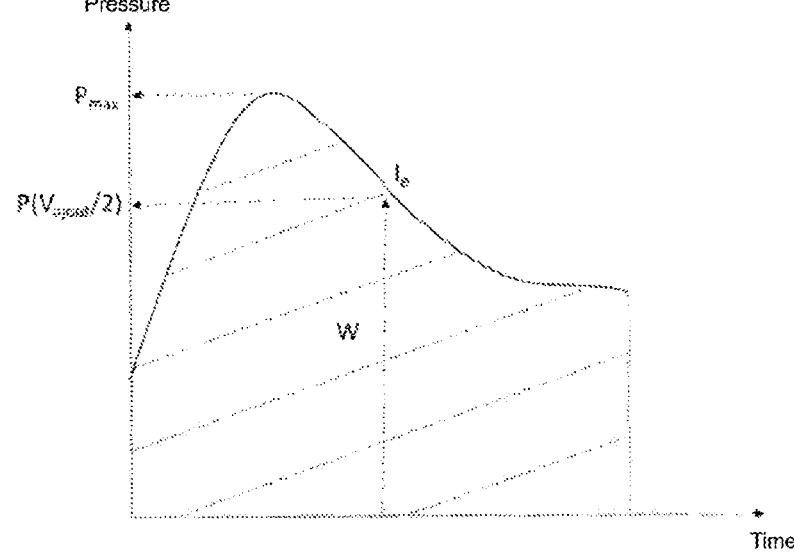

FIG. 20 shows: a) the typical shape of the pressure (kPa) over time(s) for characterizing a bread dough obtained with an alveograph; —b) the typical shape of the pressure over time for characterizing a bread dough obtained with the probe.

Figures 21, 22:
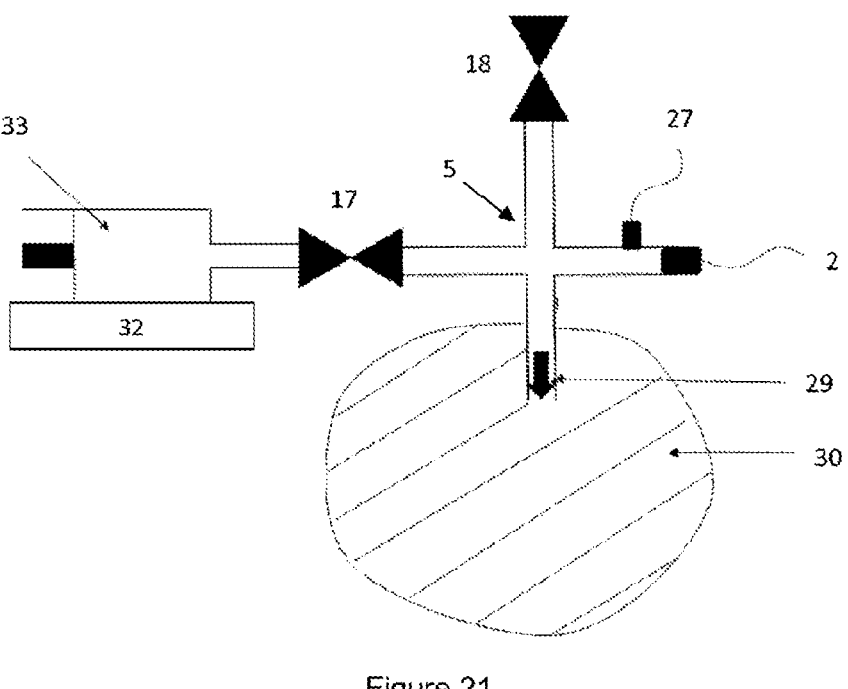

FIG. 21 shows a diagram of the measurement probe used to determine the features of the bread dough (temperature sensor (27)–pressure sensor (2)).

FIG. 22 shows the pressure variation (kPa) over time(s) for characterizing the bread dough with the probe.

Figure 23:
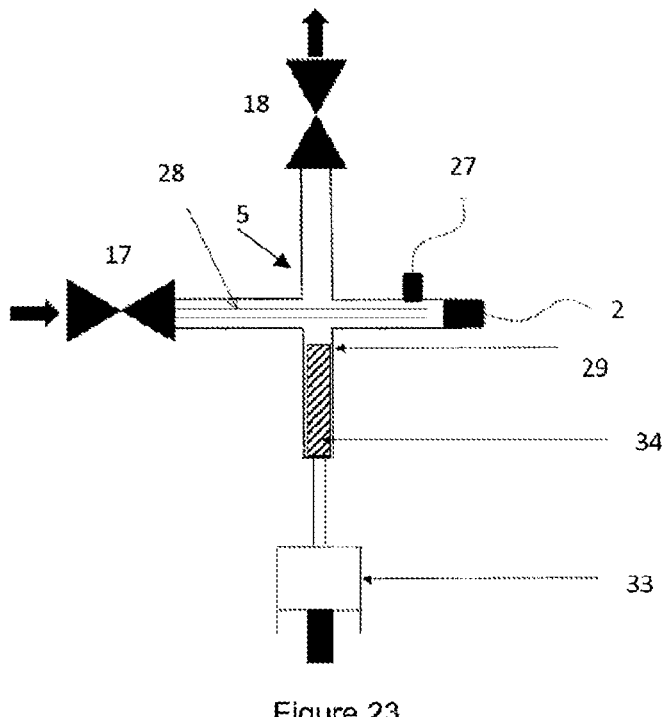

FIG. 23 shows a diagram of the measurement probe used to determine the $CO_2$ diffusion coefficient in water (temperature sensor (27)–pressure sensor (2)).

Figure 24:
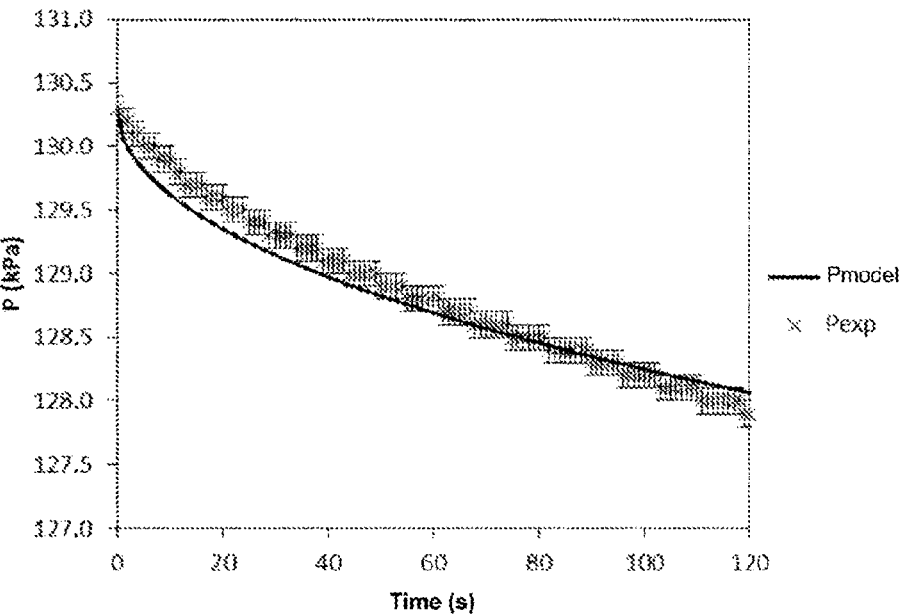

FIG. 24 shows the experimental pressure (kPa) and the pressure (kPa) determined with Equation (5) of Example 11 relating to the diffusion of $CO_2$ in water, as a function of time(s).

EXAMPLES

Example 1: Determining the $CO_2$ Production Rate of a Deformable Matrix

The $CO_2$ production rate of a cheese was determined during the first 11 days of ripening using a pressure measurement only. The measuring device used is cylindrical with a height (8)=7.0 mm and a diameter (26)=2.7 mm, of the type described in FIG. 1.

Equations useful for determining the $CO_2$ production rate of a deformable matrix.

Equation (1) is the $CO_2$ materials balance in a semi-hard cheese of the Emmental type. The material transport by diffusion and the $CO_2$ production (by propionic fermentation) are taken into account.

$$\frac{\partial C}{\partial t} - D_{CO2} \times \nabla C = r_{CO2} \tag{1}$$

With C being the $CO_2$ concentration (mol·m$^{-3}$), $D_{CO2}$ being the $CO_2$ diffusion coefficient in the cheese (m$^2$·s$^{-1}$) and $r_{CO2}$ being the $CO_2$ production rate (mol·m$^{-3}$·s$^{-1}$)

Equation 2 represents the thermodynamic equilibrium of the $CO_2$ at the interface between a gas phase and a liquid phase (water+cheese fat). The equilibrium is based on the Henry equation.

$$C = k_H^{ch} \times P_{CO2} \tag{2}$$

With $$k_H^{ch}$$

being the Henry constant (mol·m$^{-3}$·Pa$^{-1}$) and $P_{CO2}$ being the $CO_2$ pressure in the gas phase (Pa).

In order to determine the $CO_2$ production rate, the diffusion (very small $D_{CO2}$) is considered to be very slow compared with $CO_2$ production. In this case, Equation 1 becomes:

$$\frac{\partial C}{\partial t} = r_{CO2} \tag{3}$$

By combining Equation 3 with Equation 2 (Henry's law) and by integrating over time, Equation 4 is obtained, which linearly describes the pressure increase as a function of time. The pitch of the pressure increase due to $CO_2$ production as a function of time allows the $CO_2$ production rate to be obtained by knowing the Henry constant only.

$$P = P_0 + \frac{r_{CO2}}{k_h} \times t \tag{4}$$

Principle of the Measurements

The principle of the measurements involves planting the device into the cheese and monitoring the evolution of the pressure over time. By planting the device into the cheese, the volume of the gas phase decreases, which increases the pressure to a value P0 that is greater than atmospheric pressure. A pressure drop is initially observed due to the transfer of the $CO_2$ from the gas phase to the cheese until an equilibrium (according to Equation 2) is reached. Once the equilibrium is reached, the pressure will then increase due to the $CO_2$ production by the cheese and its transfer to the gas phase. The $CO_2$ production rate is determined according to Equation 4 based on this pressure increase.

Operating Conditions

An Emmental-type semi-hard cheese is used to determine the $CO_2$ production rate. For each measurement, a hole (25) is made in the cheese in order to take a core measurement (at a depth of 2 cm). In order to ensure a $CO_2$ atmosphere, the probe is scavenged with $CO_2$ for 1 minute before being planted into the cheese.

The measurements last between 1 and 2 days (10 seconds or 1 minute of pressure acquisition frequency) according to the pressure increase (that is according to the production rate). The average temperature in the piece was 20±1.5° C. Four measurements were conducted, which covered the first 11 days of ripening.

Experimental Results of Pressure Measurements

FIGS. 4 to 7 show the results of the completed pressure measurements. Each curve has the same shape: as explained above, the pressure reduces over a first time period after the pressurization due to the material transfer of $CO_2$ from the gas phase to the cheese; a ceiling is then reached, then the pressure re-increases, this time as a result of the production and the transfer of the $CO_2$ to the gas phase.

In FIGS. 4 to 7, straight lines have also been drawn during periods when the pressure re-increases. It symbolizes the data with which the $CO_2$ production rates were determined (the pitch of these straight lines allows the production rate to be computed with Equation 4).

Determining $CO_2$ Production Rates

Based on the experimental data presented in the previous paragraph, the $CO_2$ production rates were computed with Equation 4 using $3.5 \times 10^{-4}$ mol·m$^{-3}$·Pa$^{-1}$ (Chaix et al. [7]; Chaix E. [6]) as the value of the Henry constant. The results are consolidated in Table 1 and are also shown in FIG. 8.

The production rate is lowest at the start of ripening (day 2). It then gradually increases up to day 10 or it reaches a maximum and then drops again on day 11.

Table 1 shows the experimental pressure increase rates and the corresponding $CO_2$ production rates determined with Equation 4 (Henry constant equal to $3.5 \times 10^{-4}$ mol·m$^{-3}$·Pa$^{-1}$).

TABLE 1

| Measurement reference | Ripening day | Pitch of the straight line representing the pressure increase (Pa · s$^{-1}$) | $CO_2$ production rate computed with Equation 4 (mol · m$^{-3}$ · s$^{-1}$) |
|---|---|---|---|
| Measurement 1-a | 2 | $1.63 \times 10^{-2}$ | $5.70 \times 10^{-6}$ |
| Measurement 1-b | 3 | $3.74 \times 10^{-2}$ | $1.31 \times 10^{-5}$ |
| Measurement 2 | 6 | $4.84 \times 10^{-2}$ | $1.70 \times 10^{-5}$ |
| Measurement 3-a | 8 | $6.91 \times 10^{-2}$ | $2.42 \times 10^{-5}$ |
| Measurement 3-b | 9 | $7.62 \times 10^{-2}$ | $2.67 \times 10^{-5}$ |
| Measurement 4-a | 10 | $12.20 \times 10^{-2}$ | $4.26 \times 10^{-5}$ |
| Measurement 4-b | 11 | $7.09 \times 10^{-2}$ | $2.48 \times 10^{-5}$ |

Comparison with the data from the literature.

FIG. 8 shows the $CO_2$ production rate by the cheese as a function of the ripening duration (data from Table 1), as well as some values from the literature for comparison.

In general, the production rates determined in this study are consistent with the values from the literature (Huc et al.: "Influence of salt content on eye growth in semi-hard cheese studied using magnetic resonance imaging and $CO_2$ production measurements", International Dairy Journal (2014) ([1]); Acerbi et al. ([2])). Maximum production is obtained after 10 days of ripening by Huc et al. ([1]) for cheeses of the same type as that tested. By contrast, Acerbi et al. ([2]) determined maximum $CO_2$ production after 3 days of ripening.

Conclusion

The $CO_2$ production rates determined by means of the device of the invention are consistent with the values from the literature (of the order of $10^{-6}$-$10^{-5}$ mol·m$^{-3}$·s$^{-1}$). The rate increases in the first 10 days of ripening (up to a maximum of $4.26 \times 10^{-5}$ mol·m$^{-3}$·s$^{-1}$) and then decreases.

Example 2: Determining the $CO_2$ Diffusion Coefficient of a Deformable Matrix In this example, in order to determine the properties of the cheese, a device of the type defined in FIG. 1 is used, having a pressure sensor (2) for a gaseous phase with $CO_2$ only, the volume of which is small compared to that of the cheese (semi-infinite cheese, gas phase length e (corresponding to the height of the gas phase after the probe has been pushed in)<<the insertion depth of the device into the cheese L. Moreover, $CO_2$ production by fermentation is overlooked and it is considered that there is no compression of the cheese due to the pressure.

This device is a cylindrical tube with a height (8)=7.0 mm and a diameter (26)=2.7 mm made of tin. The seal is ensured by welding the pressure sensor (2) to the tin tube.

Equations useful for determining the $CO_2$ diffusion coefficient of a deformable matrix.

Under these conditions, and assuming that the transfer occurs only in one direction, the material transport equation is (Equation 1):

$$\frac{\partial C}{\partial t} - D_{CO2} \times \frac{\partial^2 C}{\partial x^2} = 0 \tag{1}$$

In order to solve this equation, it is assumed that the initial concentration of $CO_2$ in the cheese is homogeneous in the cheese and is equal to $C_0$. A pressure $P_0$ greater than atmospheric pressure is imposed at the time t=0. The limit and initial conditions are therefore:

For x=0 and t=0:

$$C = k_H^{ch} \times P_0$$

(Henry's law for determining the equilibrium at the gas/liquid interface);

For x>0 and t=0: $C = C_0$

For $$x = L: \frac{\partial C}{\partial x} = 0 \qquad (1)$$

This equation has an analytical solution for a semi-infinite plate (Tveteraas O.: "A study of pressure decay in a closed CO2-water system", Master Thesis, 2011 ([3]), Ghaderi et al.: "Estimation of concentration-dependent diffusion coefficient in pressure-decay experiment of heavy oils and bitumen", Fluid phase equilibria, 2011 ([4])):

$$P(t) = \frac{C_0}{k_h} + \left(P_0 - \frac{C_0}{k_h}\right) \times \exp\left[\frac{t}{D_{CO2}} \times \left(\frac{R \times T \times D_{CO2} \times k_h}{e}\right)^2\right] \times \qquad (2)$$
$$\text{erfc}\left[\sqrt{\frac{t}{D_{CO2}}} \times \left(\frac{R \times T \times D_{CO2} \times k_h}{e}\right)\right]$$

Based on Equation 2, it is therefore possible to describe the evolution of the $CO_2$ pressure as a function of the initial $CO_2$ concentration, of the Henry constant and of the $CO_2$ diffusion coefficient. By adjusting with experimental data of pressure measurements, it also would be possible to determine these parameters.

Please note: the function erfc ranges between 2 and 0, with values that tend towards 2 when the argument tends towards −∞ and it tends towards 0 when the argument tends towards +∞.

Based on Equation 2, two characteristic behaviors can be identified:

The behavior over a very long time:

$$\lim_{t \to +\infty} P(t) = \frac{C_0}{k_h} \qquad (3)$$

The behavior over a short time:

$$\lim_{t \to 0} P(t) = \frac{C_0}{k_h} + \left(P_0 - \frac{C_0}{k_h}\right) \times \left[1 - \frac{2}{\sqrt{\pi}} \times \frac{\sqrt{t}}{\sqrt{D_{CO2}}} \times \frac{R \times T \times D_{CO2} \times k_h}{e}\right] \qquad (4)$$

Equation 4 is derived from the product of the limits of the functions exp and erfc:

$$\left(\lim_{x \to 0} \exp(x) = 1 \text{ and } \lim_{x \to 0} \text{erfc}(x) = 1 - \frac{2}{\sqrt{\pi}} \times x\right).$$

Equation 3 provides information concerning the oversaturation of the cheese when the pressure has stabilized over a very long time. Nevertheless, the behavior over a very long time is difficult to use in practice since the $CO_2$ production is no longer negligible (depending on the ripening duration and the features of the cheese).

Equation 4 describes the behavior over a short measurement time. In reality, this equation can be provided in the form of a straight line (Equation 5).

$$\lim_{t \to 0} P(t) = \qquad (5)$$
$$\frac{C_0}{k_h} + \left(P_0 - \frac{C_0}{k_h}\right) \times \left[1 - \frac{2}{\sqrt{\pi}} \times \frac{\sqrt{t}}{\sqrt{D_{CO2}}} \times \frac{R \times T \times D_{CO2} \times k_h}{e}\right] =$$
$$P_0 - \left(P_0 - \frac{C_0}{k_h}\right) \times \frac{2}{\sqrt{\pi}} \times \frac{\sqrt{t}}{\sqrt{D_{CO2}}} \times \frac{R \times T \times D_{CO2} \times k_h}{e}$$

$$\lim_{t \to 0} P(t) = b - a \times \sqrt{t} \qquad (6)$$

With $b = P_0$ $$a = -\left(P_0 - \frac{C_0}{k_h}\right) \times \frac{2}{\sqrt{\pi}} \times \frac{R \times T \times \sqrt{D_{CO2}} \times k_h}{e}$$

Equation 6 provides a second relation between $C_D$, $k_H$ and $D_{CO2}$.

Seal Measurement

Several welds were produced between the pressure sensor (2) and the upper end (1) of the device. 2 sealing tests are carried out each time: (i) the shape of the $CO_2$ pressure reduction curve and (ii) by immersing the probe into water and by injecting air using a syringe.

FIG. 9 compares the shape of the $CO_2$ pressure reduction curves with a hermetic or a non-hermetic probe. It can be clearly seen that with a non-hermetic probe, the pressure reduction is much faster and that the pressure returns to its initial value after a few minutes.

Identifying the Materials for Constructing the Probe $CO_2$ pressure measurements were carried out with the device of the invention, and with a piece of cheese and without cheese but with a plastic plug (not previously saturated with $CO_2$). FIG. 10 compares the results obtained in both cases (with the device of the invention with a piece of cheese shown as dashes, and without cheese with a plastic plug to close the lower end of the device shown as squares). It can be seen that with a plastic device, the $CO_2$ pressure quickly reduces due to the transfer of $CO_2$ into the plastic, which illustrates that it is imperative for materials to be used that do not absorb the gas of interest (the $CO_2$ in this case).

Principle of the Pressure Measurements

The principle involves planting the device as shown in FIG. 1 in a food matrix. By planting the tube in the cheese, the volume of the gas phase decreases, which increases the pressure to a value $P_0$ that is greater than atmospheric pressure. A pressure drop is then observed in accordance with Equation 2.

In order to provide a $CO_2$ atmosphere, the device is scavenged with $CO_2$ for 1 minute before being planted into the cheese.

$CO_2$ pressure measurements were carried out with the probe with a semi-hard cheese of the Emmental type after 2 months of ripening. Given the production date of the cheese, it is considered that there is no longer any $CO_2$ production. The average temperature in the piece was 19.7° C.

The probe is planted in the core of the cheese (at a depth of approximately 2 cm) and a bracket is used to wedge the probe. The measurements were carried out over a duration of approximately 10 min (600 s) with a pressure measurement every 10 seconds. Such an experiment duration is reasonable with a fermentable cheese without the $CO_2$ production significantly modifying the pressure measurements.

Results and Discussion

Experimental Results of Pressure Measurements

FIG. 11 shows the experimental results of the obtained pressure measurements. In all cases, the pressure reduces over time in accordance with Equation 2, which confirms that $CO_2$ transfers from the gas phase to the cheese. The shape of the curves is the same for all the measurements, irrespective of the location of the measurement and the imposed initial pressure.

The aim is to determine the $CO_2$ diffusion coefficient in the cheese and the initial $CO_2$ concentration. It is considered that the Henry constant $k_H$ is known and is equal to $3.5 \times 10^{-4}$ mol·m$^{-3}$·s$^{-1}$ (Chaix et al. [7]). The 2 parameters are obtained by adjusting Equations 2 and 6 with the experimental data. In order to use Equation 2, the height of the gas phase e needs to be known. This parameter is obtained with the initial height h (7.0 mm) and the imposed initial pressure $P_0$ according to Equation 7.

$$e = \frac{h \times p_{atm}}{P_0} \quad (7)$$

FIG. 9 compares the model with the experimental data (Measurement 3). 0.5% error bars were used for the experimental values. The model is in good agreement with the experimental values with a $CO_2$ diffusion coefficient of $2.6 \times 10^{-9}$ m$^2$·s$^{-1}$ and a dissolved $CO_2$ concentration of 26 mol·m$^{-3}$. Given the value of the Henry constant, such a concentration indicates that the cheese is under-saturated with $CO_2$, which is consistent after more than 2 months of ripening and with a cheese in contact with the ambient air during certain periods.

Table 2 summarizes the results obtained and compares them with the data from the literature. The diffusion coefficients obtained range between $2.6 \times 10^{-10}$ and $5.7 \times 10^{-10}$ m$^2$·s$^{-1}$. These values are consistent with those from the literature (Acerbi et al. [5]). Table 2 shows the values of the adjusted diffusion coefficients ($k_H = 3.5 \times 10^{-4}$ mol·m$^{-3}$·Pa$^{-1}$) and the value from the literature.

TABLE 2

| Reference | $C_0$ (mol · m$^{-3}$) | Table |
|---|---|---|
| Measurement 1 | 26 | $3.0 \times 10^{-10}$ |
| Measurement 2 | 25 | $5.7 \times 10^{-10}$ |
| Measurement 3 | 26 | $2.6 \times 10^{-10}$ |
| Average | 26 | $3.8 \times 10^{-10}$ |
| Acerbi et al [5] | — | $6.8 \times 10^{-10}$ |

Conclusion

Based on measurements of $CO_2$ pressure variation in a gas phase in contact with a food matrix (cheese), it was possible to determine certain features of the food matrix (initial $CO_2$ concentration and $CO_2$ diffusion coefficient) by adjusting a model with the experimental data.

The measurements are carried out for 10 minutes. Several experimental precautions have been set forth:

The cheese must not be left in contact with the open air in order to avoid desolubilization of the $CO_2$, which alters the quality of the adjusted parameters.

Plastic materials must not be used for the design of the probe since these materials absorb $CO_2$.

A fully metal probe was manufactured in the laboratory. Assuming the known Henry constant ($3.5 \times 10^{-4}$ mol·m$^{-3}$·Pa$^{-1}$), it has been determined that the average value of the diffusion coefficient is $3.8 \times 10^{-10}$ m$^2$·s$^{-1}$. This value is in good agreement with the results from the literature.

Example 3: Determining the Material Transport Properties of a Deformable Matrix by Means of the Device of the Invention In this example, in order to determine the properties of the cheese, a device of the type defined in FIG. 1 is used.

Irrespective of the transport property to be determined, the measurement principle remains the same as for the previous examples, and it is described below:

The device, in the open air, is scavenged by the gas of interest, in this case $CO_2$. The valve (18) allowing said gas to exit the device is open, the valve (17) allowing said gas to enter the device is also open.

2) A hole (25) is made in the matrix to be analyzed, as in the present example, whether it is a food matrix or another material, in order to be able to take the core measurement if required. This hole can be made with a drill bit, for example.

3) The device, with the scavenging system (6) operating, that is, with the gas intake valve (17) and the gas outlet valve (18) open, is planted into the matrix to be analyzed. It is planted at a height (22), which is at least 1 mm in the matrix (in order to comply with certain computation hypotheses for data processing) and preferentially at a height (22)>3 mm, as shown in FIG. 14.

The open face of the probe must be that by which the probe is planted into the matrix.

The probe is quickly inserted into the matrix.

4) The scavenging system (6) is maintained for a few tens of seconds with the probe planted in the cheese to ensure that the matrix is only in contact with the gas of interest.

This time must be close to the time that separates the production of the hole (25) and the production of the probe.

5) Once the scavenging is complete, the valve (18) allowing said gas to exit the device is closed.

6) The gas intake valve (17) then feeds the gaseous chamber (5) in contact with the matrix until the desired pressure (pressure pulse) is quickly reached. The pressure to be reached is between −1 kPa and +200 kPa, preferentially +10-15 kPa.

7) Once the desired pressure is reached, the valve (17) is closed. The valve (18) remains closed. The pressure measurement then begins with the valves (17) and (18) closed for the entire duration of the analysis.

Example 4: Experimental Determination of the Viscosity of a Cheese

In this example, in order to determine the mechanical properties of the cheese, in particular its viscosity, a device of the type defined in FIG. 2 is used, having an extension that is formed by a cylindrical tube perforated on the sides and at its lower end.

Equations Useful for Determining Viscosity

The viscosity and the pressure are connected to the deformation of the radius of the cylinder (the latter is assumed to be infinite) according to Equation (1).

$$P_{cylinder} - P_{atm} = 2 \times \mu \times \frac{dR}{R} \times \frac{1}{dt} \qquad (1)$$

With $P_{cylinder}$ being the pressure (Pa) in the gas filled cylinder, $P_{atm}$ being the atmospheric pressure (Pa), $\mu$ being the viscosity of the cheese (Pa·s), R being the radius of the cylinder (m) and dt being the measurement time interval(s).

Principle for Determining Viscosity

Experimentally, a cylindrical hole is hollowed out of the cheese and the evolution of the pressure over time following an overpressure is measured. In accordance with the ideal gas law and by neglecting the material transfer relative to the mechanics, a pressure reduction corresponds to an increase in the volume of the cylinder that can be related to an increase in the radius of the cylinder (that is, the variation in the radius of a circle is proportional to the surface variation to the power of ½, Equation (2)).

$$\frac{\Delta R}{R} = \frac{P_1^{1/2} - P_2^{1/2}}{P_1^{1/2}} \qquad (2)$$

With $P_1$ being the pressure in the cylinder at the instant $t_1$ (Pa) and $P_2$ being the pressure in the cylinder at the instant $t2>t1$ (Pa).

The measurements are carried out with a semi-hard cheese of the Emmental type. The gas used to take these measurements is nitrogen, which has low solubility in matrices with a lot of water (this is the case of the studied cheese).

The probe extension is 20 mm high. In order to take the measurements, a 60 mm high cylindrical hole is hollowed out with a small drill bit and then the probe is pushed into the hole until it comes into abutment with the cap that will seal the system from the outside. Two metal weights (500 g each) are then installed in order to hold the probe in position.

Before the measurement is taken, the gaseous chamber is scavenged by nitrogen for approximately 1 min. An overpressure ranging between +15 and +35 kPa is then imposed and the pressure is measured for approximately 10 minutes for each measurement with a time interval of 1 second.

Results and Discussion

Throughout the entire duration of the analysis, the pressure has reduced due to the increase in volume of the previously hollowed out cylindrical hole and also in the initial instants of the analysis of the transfer of the gas from the gas phase to the cheese. FIG. 15 shows a typical shape of the pressure over time.

The viscosity was determined by considering the pressure values every minute, since during this time interval the pressure hardly changes (FIG. 15). At the beginning of the analysis, the computed viscosity is low for this type of cheese and it increases over time (FIG. 13). This behavior is derived from the pressure that reduces both due to the increase in volume according to the ideal gas law and also due to the transfer of the gas into the cheese. After a few minutes (approximately 5 min), the material transfer becomes very low (the surface of the cheese in contact with the gaseous chamber is saturated with nitrogen) and negligible relative to the mechanical behavior and the computed viscosity becomes constant at a value of approximately $2.5 \times 10^8$ Pa·s, in good agreement with the literature (Garnet et al., 2016 [9]).

Example 5: Determining the Mechanical Properties of a Deformable Matrix by Means of the Device of the Invention In order to determine the mechanical properties, the measuring device is used with an extension (12), as shown in FIG. 2.

The principle of the measurement of the mechanical properties is described below. It differs depending on whether the property to be determined is the viscosity or the fracture point.

Determining Viscosity

1) The probe with its extension (12), in the open air, is scavenged by gas. Valve (17) is open, valve (18) is also open. The gas used for this measurement preferably is a gas that is poorly soluble in the matrix to be analyzed in order to measure mechanical properties and not transport properties. For example, nitrogen $N_2$ is preferably used for matrices with a lot of water (this is the case of cheeses, for example), in order to limit its transfer into the matrix to be analyzed.

2) A preferably cylindrical hole (25) is made in the matrix to be analyzed. It preferably has a minimum height (23) of 60 mm. This hole (25) can be produced with a drill bit, for example.

3) The probe with its extension (12), with the scavenging system (6) operating, that is, with valves (17) and (18) open, is inserted into the hole (25) in the matrix to be analyzed, as shown in FIG. 3.

It is inserted so that the system (19) for sealing the extension (12) is positioned in order to prevent gas leaks.

A free gaseous chamber (5) must be present between the surface of the matrix to be analyzed and the extension (12) of the probe.

4) The scavenging system (6) is maintained for a few tens of seconds with the probe planted in the cheese to ensure that the matrix is only in contact with the gas of interest.

5) Once the scavenging is complete, the outlet valve (18) is closed.

6) Valve (17) feeds the gaseous chamber (5) in contact with the matrix until the desired pressure (pressure pulse) is quickly reached. The pressure to be reached ranges between +1 kPa and +150 kPa.

7) Once the desired pressure has been reached, the intake valve (17) is closed. Valve (18) remains closed. The pressure measurement then begins with valves (17) and (18) closed for the entire duration of the analysis (a few minutes).

Determining the Fracture Point

The operating principle of the probe for determining the fracture point is as follows:

1) The probe with its extension (12), in the open air, is scavenged by gas. Valve (17) is open, valve (18) is also open.

The gas used for this measurement preferably is a gas that is poorly soluble in the matrix to be analyzed in order to measure mechanical properties and not transport properties. For example, using nitrogen N2 is preferable for matrices with a lot of water, such as cheeses, for example, in order to limit its transfer into the matrix to be analyzed.

2) A hole (25), optionally cylindrical, is made in the matrix to be analyzed. This hole (25) can be produced with a drill bit, for example.

3) The device with its extension (12), with the scavenging system (6) operating, that is, with valves (17) and (18) open, is inserted into the hole (25) in the matrix to be analyzed.

It is inserted so that the means (19) for sealing the extension (12) is positioned in order to prevent gas leaks.

A free gaseous chamber (5) must be present between the surface of the matrix to be analyzed and the extension (12) of the probe, as shown in FIG. 3.

4) The scavenging system (6) is maintained for a few tens of seconds with the probe planted in the cheese to ensure that the matrix is only in contact with the gas of interest.

5) Once the scavenging is complete, the outlet valve (18) is closed.

6) Valve (17) feeds the gaseous chamber (5) in contact with the matrix to be analyzed. The pressure progressively increases until the matrix is "fractured", from which moment the pressure returns to atmospheric pressure.

Example 6: Determining the Henry Constant of $CO_2$ with Regard to a Cheese

1. Theory

In order to determine the Henry constant $k_H$ of a gas with regard to a matrix to be characterized, a piece of the matrix with a known volume $V_{matrix}$ is placed in a closed volume enclosure $V_{enclosure}$ containing only the gas of interest. The gas phase in the measurement enclosure has a volume $V_{gas}$ ($V_{gas}=V_{enclosure}-V_{matrix}$) and it must be in equilibrium with the matrix to be analyzed at a pressure $P_{ini}$.

An initial overpressure $P_0$ is then imposed and the return to equilibrium is measured at a new pressure $P_{eq}$ (due to the transfer of some of the gas to the matrix to be analyzed). Under these conditions, assuming that the temperature is constant and that the thermodynamic equilibrium can be described by Henry's law, the Henry constant is determined with Equation (1).

$$k_H = \frac{(P_0 - P_{eq}) \times V_{gas}/R \times T}{V_{matrix}} \times \frac{1}{P_{eq} - P_{ini}} \tag{1}$$

Where $P_0$ is the imposed overpressure (Pa), $P_{eq}$ is the equilibrium pressure (Pa), $V_{gas}$ is the volume of the gas phase ($m^3$), $V_{matrix}$ is the volume of the matrix to be analyzed ($m^3$), R is the ideal gas constant, T is the temperature (K) and $P_{ini}$ is the initial equilibrium pressure (Pa).

Material and Method

A block of cheese, stored for several months at 4° C., and then for several weeks at 19° C., was used to take the measurement. A piece of cheese weighing 0.33 g was taken for the analysis. Since the density of the cheese is 1,120 kg·m$^{-3}$, the volume of the piece of cheese was 0.3 cm$^3$. The $CO_2$ originated from a gas cylinder (purity>99.99%).

The measurement was carried out with the probe shown in FIG. 16. It is provided with a pressure sensor (2) and a sensor (27) for measuring the temperature of the gaseous phase inside the probe. Two valves (an intake valve (17) and an outlet valve (18)) allow the probe to be scavenged with the gas of interest. An internal tube (28) was added into the probe in order to ensure that the scavenging is properly carried out throughout the volume of the probe. The last part of the probe is made up of a cylindrical tube (29), into which the piece of matrix (30) to be analyzed was inserted and which was then hermetically sealed. The probe is entirely metallic and its void volume is 1.3 cm$^3$.

Experimentally, the following procedure was applied:
the piece of matrix (30) to be analyzed (cheese in this case) is inserted into the probe;

the probe is closed;
the probe is scavenged with the gas of interest ($CO_2$ in this case) for several seconds (ensuring that the temperature remains constant and equal to the ambient temperature);
by closing the gas outlet valve (18), an overpressure is imposed in the gaseous chamber (5);
the gas intake valve (17) is closed. This results in the gas transferring to the matrix (30) to be analyzed, the pressure reduces and then stabilizes at a value $P_{ini}$;
in the same way, a second overpressure $P_0$ is imposed and the stabilization of the pressure to a value $P_{eq}$ that is greater than the first stabilization pressure is awaited.

FIG. 17 shows the overall shape of the pressure variation during the experiment for determining the Henry constant.

3. Results

The following experimental pressures were measured at a temperature of 18.5° C.:
$P_{ini}$=99.1 kPa
$P_0$=126.4 kPa
$P_{eq}$=119.2 kPa The Henry constant of $CO_2$ with regard to cheese determined with Equation (1) in this case is equal to $5.0\times10^{-4}$ mol·m$^{-3}$·Pa$^{-1}$. This value is of the same order of magnitude as the values from the literature (Acerbi ([2]); Jakobsen ([8])). The difference from the literature can originate from differences in the composition of the cheese or in the ripening duration, which was not the same.

Example 7: Determining the Henry Constant of $CO_2$ with Regard to Water

1. Theory

Equation (1) explained in Example 6 was also used to determine the Henry constant of $CO_2$ in water.

2. Material and Method

Distilled water was used and the $CO_2$ originated from a gas cylinder (purity >99.99%). The experiments were carried out in a temperature regulated enclosure set to 18.5° C.

The measurement was carried out with the probe shown in FIG. 16 of Example 7. It is provided with a pressure sensor (2) and a sensor (27) for measuring the temperature of the gaseous phase inside the probe. Two valves ((17), (18)) allow the probe to be scavenged with the gas of interest. An internal tube (28) has been added into the probe in order to ensure that the scavenging is fully carried out throughout the volume of the probe. The last part of the probe is made up of a cylindrical tube (29), into which the water to be analyzed was inserted and which was then hermetically sealed. The probe is entirely metallic and its void volume is 1.3 cm$^3$.

Experimentally, the following procedure was applied:
1.0 mL of water is injected into the probe;
the probe is closed;
the probe is scavenged with the gas of interest ($CO_2$ in this case) for several seconds;
by closing the gas outlet valve (18), an overpressure is imposed in the gaseous chamber (5);
the gas intake valve (17) is closed. This results in the gas transferring to the water, the pressure reduces and then stabilizes at a value $P_{ini}$ in the same way, a second overpressure $P_0$ is imposed and the stabilization of the pressure to a value $P_{eq}$ that is greater than the first stabilization pressure is awaited.

3. Results

The following experimental pressures were measured at a temperature of 18.5° C.:

$P_{ini}$=99.6 kPa $P_0$=103.0 kPa $P_{eq}$=101.0 kPa

The Henry constant of $CO_2$ with regard to the water determined with Equation (1) is equal to $3.5\times10^{-4}$ mol·$m^{-3}$·$Pa^{-1}$. This value is very close to that of the literature (Sander, 2015 ([13]); Versteeg ([14])) with an 8% deviation and appears to confirm the use of the probe for determining the Henry constant.

Example 8: Determining the Viscosity of a Bitumen and of a Bread Dough

1. Theory

The principle for determining the viscosity of a matrix involves applying an overpressure in a gaseous phase in contact with the matrix and measuring the pressure variation. Indeed, the pressure reduces over time due to the increase in volume of the gaseous phase. In this case, a gas needs to be selected that hardly reacts or solubilizes in the matrix or the elements used to provide the seal over the duration of the measurement, so that the entire pressure variation is attributable to the variation in volume of the matrix.

For a cylindrical geometry, and assuming that the variation in volume is only due to a variation in the radius of the gaseous cylinder, the pressure can be connected to the viscosity and to the radial deformation with Equation (1).

$$P - P_{atm} = 2 \times \mu \times \frac{dR}{R} \times \frac{1}{dt} \qquad (1)$$

Where P is the pressure in the gas phase in contact with the matrix to be analyzed (Pa), $P_{atm}$ is the surrounding atmospheric pressure at the time of the test (approximately equal to 101.325 Pa at sea level), u is the viscosity of the matrix to be analyzed (Pa·s), R is the radius of the gaseous cylinder created in the matrix to be analyzed (m) and t is the time(s). Ideally, the initial imposed pressure must be high compared to the pressure variation of the atmosphere in the matrix during the measurement.

The relative variation of the radius of the gaseous phase $$\frac{dR}{R}$$

corresponds to a variation in volume at an exponent of ½ (since it is only radial deformation). In accordance with the ideal gas law (Equation (2)), the relative variation of the radius of the gaseous phase therefore can be determined with the pressure variation in the gas phase with Equation (3).

$$P \times V = n \times R \times T \qquad (2)$$

Where V is the volume of the gaseous cylinder in the matrix to be analyzed ($m^3$), n is the amount of gas (mol), R is the constant of the ideal gases (J·$mol^{-1}$·$K^{-1}$) and T is the temperature (K).

$$\frac{\Delta R}{R} = \frac{P_1^{1/2} - P_2^{1/2}}{P_1^{1/2}} \qquad (3)$$

Where $P_1$ is the pressure at the time $t_1$ (Pa) and $P_2$ is the pressure at the time $t_2 > t_1$ (Pa).

2. Material and Methods

The viscosity measurements were carried out on the commercially available Azalt 70/100 (Total) bitumen and on a bread dough with a commercial composition. The measurements were carried out with nitrogen (purity >99.99%).

The probe described in FIG. 18 was used to take the measurements. It is provided with a pressure sensor (2) and a temperature sensor (27). Two valves (an intake valve (17) and an outlet valve (18)) allow the probe to be scavenged with the gas of interest. An internal tube (28) was added into the probe in order to ensure that the scavenging is properly carried out throughout the volume of the probe. The fourth part of the probe is made up of a cylindrical tube (29) that is open at its end and is inserted into the matrix to be analyzed (30) in order to allow the gas to come into contact with the matrix. A plug (31) provides the seal with the matrix to be analyzed (30). The measurements were carried out in a temperature regulated chamber set to 22±1° C. for the bitumen and 19±1° C. for the bread dough.

Experimentally, the following protocol was applied:

a 60 mm high and 7.5 mm diameter cylindrical cavity is hollowed out of the matrix to be analyzed (30) using a drill bit;

the probe is inserted into the cylindrical cavity as illustrated in FIG. 18;

an overpressure of approximately +2 kPa is imposed with nitrogen by conveying gas through the intake valve (17) and by closing the outlet valve (18);

the gas intake valve (17) is closed and the pressure is measured for several minutes with an acquisition frequency of 1 second.

3. Results

With the bitumen, nine tests were carried out and the results are consolidated in FIG. 19. The measurements are reproducible and the average value of the viscosity is $5.6\pm0.6\times10^5$ Pa·s. This value is of the same order of magnitude as that from the literature ($4.34\times10^5$ Pa·s at 22° C. (Mouazen, 2011 ([11]))) and the difference can originate from the slight temperature deviation (measurements carried out with the probe at 21.4° C.).

In the same way with the bread dough, a viscosity of $1.0\times10^5$ Pa·s was determined at 19.5° C. This value is also in good agreement with the literature (Bloksma, 1975 ([10])).

Example 9: Application of the Probe for Characterizing the Bread Dough Like an Alveograph With the probe, it is possible to determine certain features of a bread dough like an alveograph. The principle, which is similar to that of an alveograph, involves continuously bringing gas into contact with the bread dough, which leads to an increase in the pressure and a deformation of the bread dough. The main difference with the alveograph originates from the fact that the measurements with the probe take place in a core in a block of dough (which allows the actual atmosphere of the bread dough to be preserved).

FIG. 20 shows the shape of a pressure curve obtained with the probe and the comparison with the alveograph. In FIG. 20-*a*, corresponding to the alveograph, several data items can be obtained for characterizing the bread dough:

the maximum overpressure P characterizes the resistance to deformation (toughness of the dough);

the area under the curve W allows the strength of the flour to be characterized, it is called baking strength;

the elasticity index characterizes the elastic resistance;

the abscissa at breakpoint L provides information concerning the extensibility of the bread dough.

With the probe (FIG. 20-*b*), similar information can be obtained (except the abscissa at breakpoint L, which is not observed since the measurement occurs on a large block of bread dough and not on a film):

The maximum overpressure $P_{max}$ characterizes the resistance to deformation;

The area under the curve (after a pre-defined measurement time) W allows the strength of the flour to be characterized;

The elasticity index characterizes the elastic resistance.

Material and Method

The measurements were carried out with a bread dough with a commercial composition and with air. The probe used for the measurements is described in FIG. 21. It is provided with a pressure sensor and a temperature sensor. Two valves (an intake valve (17) and an outlet valve (18)) allow the gas to enter and to exit. The probe is also made up of a cylindrical tube (29), which is open at its end that is inserted into the matrix (30) to be analyzed in order to allow the gas to come into contact with the matrix (30). A syringe pump (32) and a syringe (33) allow the continuous arrival of the gas to be controlled at a controlled flow rate.

The following experimental procedure was adopted:

The probe is planted into a block of bread dough.

The gas is continuously injected using the syringe pump at a flow rate of 0.8 mL·min$^{-1}$ for 2 minutes The pressure is measured throughout the duration of the analysis with an acquisition frequency of 1 second. The temperature is also measured.

3. Results

FIG. 22 shows an example of a signal obtained with the probe for characterizing the bread dough. The pressure variation is very similar to that obtained with an alveograph, firstly with a pressure increase that characterizes the deformation resistance of the dough ($P_{max}$=0.7 kPa) and then with a gradual pressure reduction that reflects the extensibility of the bread dough.

Depending on the maximum measured pressure and the gradual pressure reduction, the quality of the bread dough thus can be qualified.

Example 10: Determining the $CO_2$ Diffusion Coefficient in Water

1. Theory

The principle of the measurement for determining the diffusion coefficient of a gas dissolved in a food matrix involves applying an overpressure in a gas phase (with the gas of interest only) in contact with the matrix to be analyzed. Due to the transfer of the gas from the gaseous phase to the matrix (according to Henry's law) and then its diffusion into the matrix (according to Fick's law), the pressure reduces in the gas phase. The evolution of this pressure reduction can be connected to the properties of the matrix with regard to the gas of interest, in particular the diffusion coefficient with Equation (1).

$$P(t) = \frac{C_0}{k_h} + \left(P_0 - \frac{C_0}{k_h}\right) \times \exp\left[\frac{t}{D_{CO2}} \times \left(\frac{R \times T \times D_{CO2} \times k_h}{e}\right)^2\right] \times \tag{1}$$
$$\operatorname{erfc}\left[\sqrt{\frac{t}{D_{CO2}}} \times \left(\frac{R \times T \times D_{CO2} \times k_h}{e}\right)\right]$$

With P being the pressure (Pa) over time t(s), $C_0$ being the initial concentration of dissolved gas in the matrix to be analyzed (mol·m$^{-3}$), $k_h$ being the Henry constant (mol·m$^{-3}$·Pa$^{-1}$), $P_0$ being the initial imposed overpressure (Pa), $D_{CO2}$ being the diffusion coefficient of the gas in the matrix to be analyzed (m$^2$·s$^{-1}$) and e being the height of the gas phase in contact with the matrix to be analyzed (m).

2. Material and Method

Distilled water was used and the $CO_2$ originated from a gas cylinder (purity >99.99%). The experiments were carried out at a temperature of 20.0° C.

The measurement was carried out with the probe shown in FIG. 23. It is provided with a pressure sensor (2) and a sensor (27) for measuring the temperature of the gaseous phase inside the probe. Two valves (an intake valve (17) and an outlet valve (18)) allow the probe to be scavenged with the gas of interest. An internal tube (28) has been added into the probe in order to ensure that the scavenging is fully carried out throughout the volume of the probe. The last part of the probe is made up of a cylindrical tube (29), in which the water to be analyzed (34) was inserted using a syringe (33) and which was then hermetically sealed. The probe is entirely metallic and its void volume is 1.3 cm$^3$.

Experimentally, the following procedure was applied:

Scavenging of the probe is started by opening the gas intake and outlet valves;

1.0 mL of water is injected into the probe with the syringe;

The scavenging, with water in the probe, is maintained for 1 minute;

The gas outlet valve is closed;

By closing the gas outlet valve, an overpressure $P_0$ is imposed in the gaseous chamber (5);

the supply of gas is cut by closing the gas intake valve and the pressure measurement is started for 120 seconds.

The $CO_2$ diffusion coefficient in water was assessed considering that the Henry constant of $CO_2$ in water is equal to 3.4×10$^{-4}$ mol·m$^{-3}$·Pa$^{-1}$ and by assuming that the surface of the water is initially saturated with $CO_2$ due to the $CO_2$ scavenging for 1 minute before the start of the measurement.

3. Results

FIG. 24 shows the agreement between the experimental pressure values and those determined with the model (Equation (5)) for a diffusion coefficient of 1.6×10$^{-9}$ m$^2$·s$^{-1}$. It should be noted that the model is in good agreement with the experimental values, which confirms that Equation (5) clearly describes the transfer and the diffusion of the $CO_2$ in water. This value of the $CO_2$ diffusion coefficient in water is in good agreement with the values of the literature with 11% deviation (Moultos et al., 2014 ([12]); Versteeg, 1988 ([14])).

LISTS OF REFERENCES

1. Huc et al.: "Influence of salt content on eye growth in semi-hard cheese studied using magnetic resonance imaging and CO2 production measurements", International Dairy Journal (2014).
2. Acerbi et al.: "Impact of salt concentration, ripening temperature and ripening time on CO2 production of semi-hard cheese with propionic acid fermentation", Journal of Food Engineering, 177, 72-79 (2016).
3. Tveteraas O.: "A study of pressure decay in a closed CO2-water system", Master Thesis, 2011.
4. Ghaderi et al.: "Estimation of concentration-dependent diffusion coefficient in pressure-decay experiment of heavy oils and bitumen", Fluid phase equilibria, 2011.
5. Acerbi et al.: "An appraisal of the impact of compositional and ripening parameters on CO2 diffusivity in semi-hard cheese", Food Chemistry, 2016.
6. Chaix E.: "Caractérisation et modélisation des transferts de gaz (O2/CO2) dans le système emballage/aliment en lien avec les réactions de croissance microbienne (microbiologie prévisionnelle) (Characterization and modeling of the gas transfers (O2/CO2) in the packaging/food system in relation to the microbial growth reactions (predictive Microbiology))", Thesis of the University of Montpellier 2, 2014.
7. Chaix et al.: "Oxygen and carbon dioxide solubility and diffusivity in solid food matrix: a review of past and current knowledge", Comprehensive reviews in food science and food safety, Chaix et al., 2014.
8. Jakobsen M., Nygaard Jensen P.: "Assessment of carbon dioxide solubility coefficients for semi-hard cheeses: the effect of temperature and fat content", Eur. Food Res. Technol., 229, 287-294 (2009).
9. Grenier D., Laridon Y., Le Ray D., Challois S., Lucas T.: "Monitoring of single eye growth under known gas pressure: Magnetic resonance imaging measurements and insights into the mechanical behavior of a semi-hard cheese", Journal of Food Engineering 171, 119-128, (2016).
10. Bloksma, A., Nieman, W., (1975), "The effect of temperature on some rheological properties of wheat flour doughs", Journal of Texture studies 6(3), 343-361.
11. Mouazen, M., (2011), "Evolution des propriétés rhéologiques des enrobés bitume, vers une loi vieillissement/viscosité. (Evolution of the rheological properties of coated bitumen, towards an aging/viscosity law)", École Nationale Supérieure des Mines de Paris (Higher National School of Mines, Paris).
12. Moultos, O. A., Tsimpanogiannis, I. N., Panagiotopoulos, A. Z., Economou, I. G., (2014), "Atomistic molecular dynamics simulations of CO2 diffusivity in H2O for a wide range of temperatures and pressures", The Journal of Physical Chemistry B 118(20), 5532-5541.
13. Sander, R., (2015), "Compilation of Henry's law constants (version 4.0) for water as solvent", Atmospheric Chemistry and Physics 15(8), 4399-4981.
14. Versteeg, G. F., Van Swaaij, W. P., (1988), "Solubility and diffusivity of acid gases (carbon dioxide, nitrous oxide) in aqueous alkanolamine solutions", Journal of Chemical & Engineering Data 33(1), 29-34.

The invention claimed is:

1. A measuring device for measuring physicochemical properties of gas in a deformable material in which the gas is soluble and diffusible, comprising:
   a hollow tube comprising;
   an upper end, into which a pressure sensor connected to an apparatus for recording is entirely and hermetically inserted;
   a lower end, which is in communication with said pressure sensor and which is open to allow (i) the measuring device to be inserted into said deformable material and to allow (ii) a gaseous chamber to be formed between said pressure sensor and said deformable material when said measuring device is inserted therein;
   a system for scavenging a gas from the gaseous chamber;
   at least one valve for introducing said gas into the gaseous chamber; and
   said gaseous chamber being made from a material that does not absorb said gas.

2. The device according to claim 1, wherein said material that does not absorb said gas is selected from among metal, glass, and polymer materials previously saturated with said gas or treated so as not to absorb said gas.

3. The device according to claim 1, wherein a height of said device is greater than or equal to 5 mm, and a height between a lower end of the device and the pressure sensor is greater than 1 mm.

4. The device according to claim 1, further comprising at least one clamp for holding the device in position relative to said material.

5. The device according to claim 1, further comprising an extension sealably connected with the lower end of said device.

6. The device according to claim 1, wherein said deformable material is a food matrix or a non-food matrix.

7. The device according to claim 6, wherein the food matrix is selected from a cheese product, a bakery product, a meat, a fish, a meat or fish-based product, a fruit, a vegetable, a fruit or vegetable-based product, a food paste, and mixtures thereof, and wherein the non-food matrix is selected from concrete, cement, asphalt, plaster, polymers, gels, earth, wood, silicone, coal, rocks, and mixtures thereof.

8. A method for measuring a pressure of a gas in a deformable material in which the gas is soluble and diffusible, using a measuring device as defined in claim 1, comprising:
   (a) inserting said measuring device into the deformable material;
   (b) increasing or decreasing the pressure of the gaseous chamber by at least one gas intake valve of the gas scavenging system to a desired pressure; and
   (c) measuring the pressure of the gaseous chamber.

9. The method according to claim 8, wherein said gas is selected from among carbon dioxide, nitrogen, oxygen, rare gases, volatile organic compounds, ammonia, and a mixture thereof.

10. The method according to claim 8, wherein when the pressure increases in (b), the pressure increase is carried out progressively until said deformable material is fractured.

11. The method according to claim 8, further comprising, after (a) inserting said measuring device into the deformable material, scavenging the gas from the gaseous chamber by the gas scavenging system at a constant pressure.

12. The method according to claim 8, further comprising measuring a temperature of the gaseous chamber.

13. The device according to claim 1, wherein the device comprises a measuring device for measuring, in the deformable material, at least one physicochemical property selected from among material transport properties with regard to gas and mechanical properties.

14. The device according to claim 13, wherein the at least one physicochemical property is material transport properties with regard to the gas and is selected from a diffusion coefficient, a gaseous gas/dissolved gas equilibrium constant, a dissolved gas concentration, and/or a production rate.

15. The device according to claim 13, wherein the at least one physicochemical property is the mechanical properties and is selected from elasticity, viscosity, visco-elasticity, fracture point, and combinations thereof.

16. The device according to claim 1, wherein the device comprises a measuring device for preparing or monitoring of features of materials in which a gas is likely to solubilize and diffuse.

17. The device according to claim 1, wherein the apparatus is further configured to process a signal.

18. The device according to claim 1, further comprising at least one valve for removing said gas from the gaseous chamber.

19. The device according to claim 1, wherein said hollow tube is cylindrical.

20. The device according to claim 1, further comprising:
  the deformable material, wherein the gas is soluble and
    diffusible in the deformable material.

* * * * *